US010267204B2

(12) United States Patent
Zhang

(10) Patent No.: US 10,267,204 B2
(45) Date of Patent: Apr. 23, 2019

(54) METHOD AND SYSTEM FOR EXHAUST PARTICULATE MATTER SENSING

(71) Applicant: Ford Global Technologies, LLC, Dearborn, MI (US)

(72) Inventor: Xiaogang Zhang, Novi, MI (US)

(73) Assignee: Ford Global Technologies, LLC, Dearborn, MI (US)

( * ) Notice: Subject to any disclaimer, the term of this patent is extended or adjusted under 35 U.S.C. 154(b) by 254 days.

(21) Appl. No.: 15/062,384

(22) Filed: Mar. 7, 2016

(65) Prior Publication Data

US 2017/0254251 A1    Sep. 7, 2017

(51) Int. Cl.
| | | |
|---|---|---|
| *F01N 11/00* | (2006.01) | |
| *G01M 15/10* | (2006.01) | |
| *G01N 15/06* | (2006.01) | |
| *G01N 15/00* | (2006.01) | |

(52) U.S. Cl.
CPC ......... *F01N 11/007* (2013.01); *G01M 15/102* (2013.01); *G01N 15/0606* (2013.01); *G01N 15/0656* (2013.01); *F01N 2560/05* (2013.01); *F01N 2560/20* (2013.01); *G01N 2015/0046* (2013.01)

(58) Field of Classification Search
CPC ...... G01N 15/0656; G01N 2015/0046; G01M 15/102; F01N 11/007; F01N 2560/05; F01N 2560/20
USPC ........... 73/23.31, 23.33, 31.05; 204/424–431
See application file for complete search history.

(56) References Cited

U.S. PATENT DOCUMENTS

| | | | |
|---|---|---|---|
| 2007/0089399 A1* | 4/2007 | Rhodes | F01N 3/027 60/278 |
| 2012/0118039 A1* | 5/2012 | Tsuzuki | G01N 27/4077 73/23.2 |
| 2015/0355066 A1 | 12/2015 | Zhang | |
| 2015/0355067 A1 | 12/2015 | Zhang et al. | |

OTHER PUBLICATIONS

Kubinski, David John, "Method and System for Exhaust Particulate Matter Sensing," U.S. Appl. No. 14/613,012, filed Feb. 3, 2015, 56 pages.
Yi, Jianwen James et al., "Systems and Methods for Sensing Particulate Matter," U.S. Appl. No. 14/842,573, filed Sep. 1, 2015, 41 pages.
Zhang, Xiaogang, "System for Sensing Particulate Matter," U.S. Appl. No. 14/966,408, filed Dec. 11, 2015, 40 pages.

* cited by examiner

*Primary Examiner* — Lisa M Caputo
*Assistant Examiner* — Irving A Campbell
(74) *Attorney, Agent, or Firm* — Julia Voutyras; McCoy Russell LLP

(57) ABSTRACT

Methods and systems are provided for a particulate matter sensor positioned downstream of a diesel particulate filter in an exhaust system. In one example, a particulate matter sensor assembly may include an outer stepped tube, an inner stepped tube positioned within the outer tube, and a plate having sensor element positioned inside the inner tube, the inner and the outer tube generating a step in the assembly. The step may block larger contaminants and water droplets, and thereby stopping them from impinging on the sensor element positioned within the assembly.

16 Claims, 8 Drawing Sheets

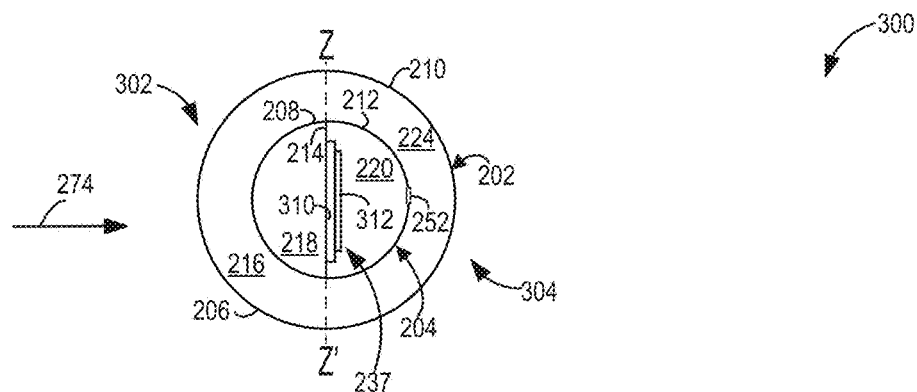
FIG. 3A
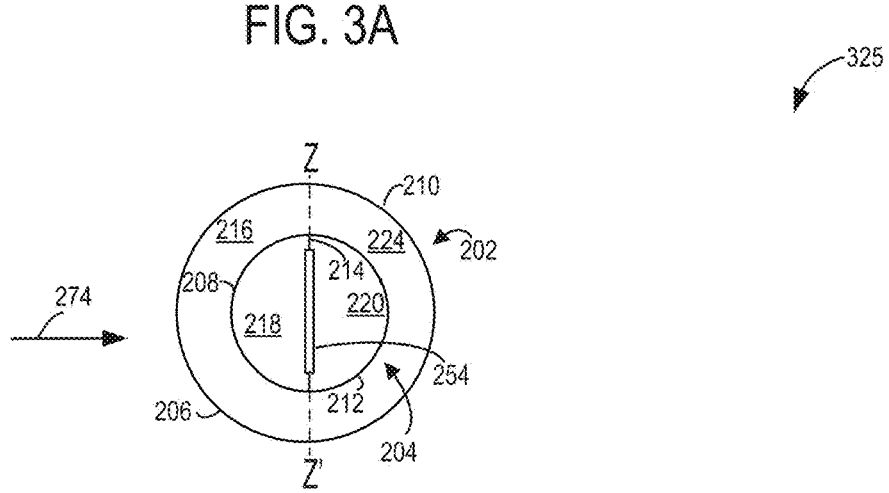
FIG. 3B
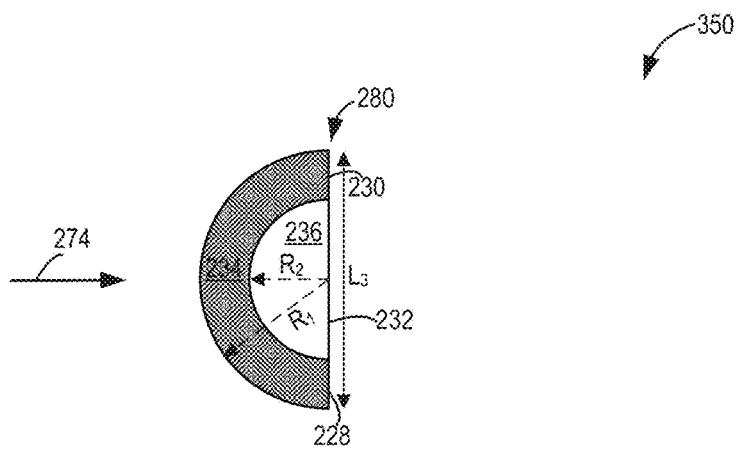
FIG. 3C
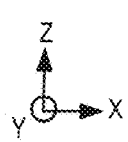

METHOD AND SYSTEM FOR EXHAUST PARTICULATE MATTER SENSING

FIELD

The present application relates to sensing particulate matter in an exhaust system.

BACKGROUND/SUMMARY

Engine emission control systems may utilize various exhaust sensors. One example sensor may be a particulate matter sensor which indicates particulate matter mass and/or concentration in the exhaust gas. In one example, the particulate matter sensor may operate by accumulating particulate matter over time and providing an indication of the degree of accumulation as a measure of exhaust particulate matter levels.

Accuracy of particulate matter sensors may be affected by non-uniform deposition of soot on the sensor due to a bias in flow distribution across the surface of the sensor. Further, particulate matter sensors may be prone to contamination from an impingement of water droplets and/or larger particulates present in the exhaust gases. This contamination may lead to errors in sensor output. Furthermore, sensor regeneration may be inadequate when a substantial quantity of exhaust gases stream across the particulate matter sensor.

The inventors herein have recognized the above issues and identified an approach to at least partly address the issues. In one example approach, a particulate matter assembly for sensing particulate matter in an exhaust passage of an engine is provided. The particulate matter assembly comprises an outer stepped tube having a first semi-circular region and a second semi-circular region, the first region being longer than the second region, an inner stepped tube coaxial to the outer stepped tube having a third semi-circular region and a fourth semi-circular region, the third region being longer than the fourth region, and a plate positioned inside the inner stepped tube having a sensor element. In this way, by coupling the outer stepped tube and the inner stepped tube, a stepped structure (hereafter referred to as a step) may be generated in the PM sensor assembly. In addition, inlets may be formed on the step to direct exhaust gas into the PM sensor assembly. As an example, inlets positioned along the step may direct exhaust in the exhaust passage in a direction opposite to the direction of exhaust flow in the exhaust passage.

As such, larger particulates in the exhaust may not be able to sufficiently reverse the flow direction and enter the PM sensor assembly via the step. Thus, the step serves to substantially block the larger particulates in the exhaust flow from impinging on the sensor element formed on the plate positioned within the assembly, thereby reducing fluctuations at the sensor due to large particulates depositing on the sensor element.

As one example, an exhaust particulate matter sensor assembly may be positioned downstream of a particulate filter in an exhaust pipe. The particulate matter sensor assembly may include a protection tube comprising an outer asymmetrical tube composed of semi-circular regions of unequal lengths. Likewise, the inner tube may include asymmetrical semi-circular regions that are positioned entirely within the outer tube. When coupled together, the difference in lengths of the asymmetrical semi-circular regions of each of the outer tube, and the inner tube may result in a step structure being created on one face of the sensor assembly. As such, the step may include inlets to direct the exhaust gas into an annular region formed between the inner and the outer stepped tube. As a consequence, the exhaust gas may be able to enter the PM sensor via the inlets in the slit by undergoing a reversal in the direction of flow. However, larger particulates and water droplets may not be able to sufficiently reverse the flow direction in order to be able enter the inlets on the step. Thus, larger particulates and/or water droplets may be blocked by the step, reducing sensor errors. Further, sensor elements positioned within the inner tube may experience a more uniform soot deposition through a direct flow impingement on the surface of the electrodes.

In this way, the step formed as a result of the asymmetry in the protection tube design may block the larger particulates and/or water droplets from entering the particulate matter sensor assembly. The technical effect of including an asymmetrical protection tube and a stepped structure in the design of the particulate matter sensor assembly is that the sensor element positioned within may be better protected from impingement of larger particulates and contaminants without adding additional components and/or filters to the particulate matter sensor assembly. Overall, the functioning of the sensor element may be improved and the sensor may be rendered more reliable.

It should be understood that the summary above is provided to introduce in simplified form a selection of concepts that are further described in the detailed description. It is not meant to identify key or essential features of the claimed subject matter, the scope of which is defined uniquely by the claims that follow the detailed description. Furthermore, the claimed subject matter is not limited to implementations that solve any disadvantages noted above or in any part of this disclosure.

BRIEF DESCRIPTION OF THE DRAWINGS

FIGS. 3A-3C show cross-sectional views of the outer and the inner tube, the plate, and a step formed in the PM sensor assembly along three different cross-sectional planes.

DETAILED DESCRIPTION

Figure 1:
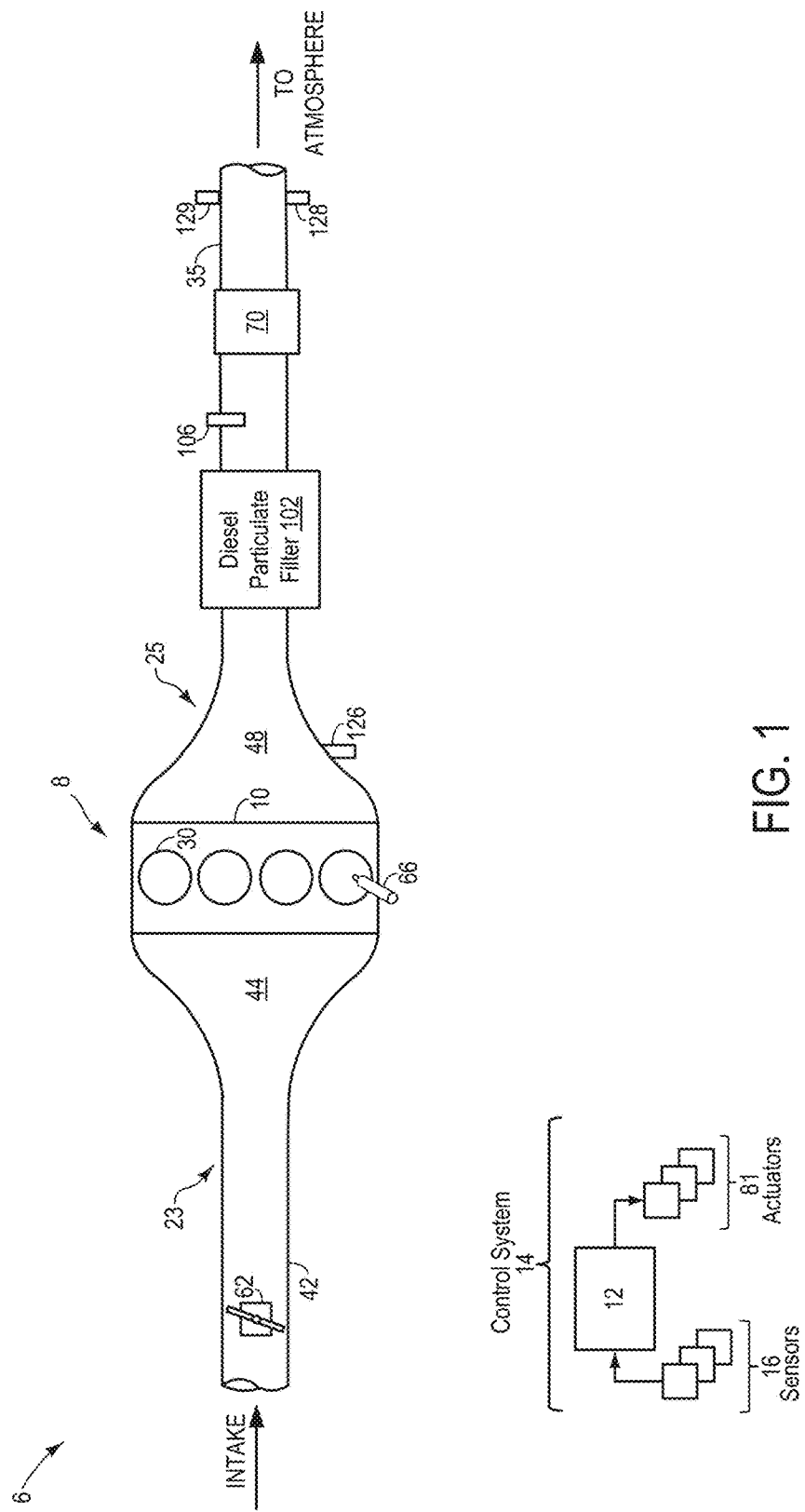
FIG. 1 shows a schematic diagram of an engine and an associated particulate matter (PM) sensor assembly positioned in an exhaust flow.

The following description relates to systems and methods for sensing particulate matter (PM) in an exhaust flow of an engine system, such as the engine system shown in FIG. 1.

Figure 2:
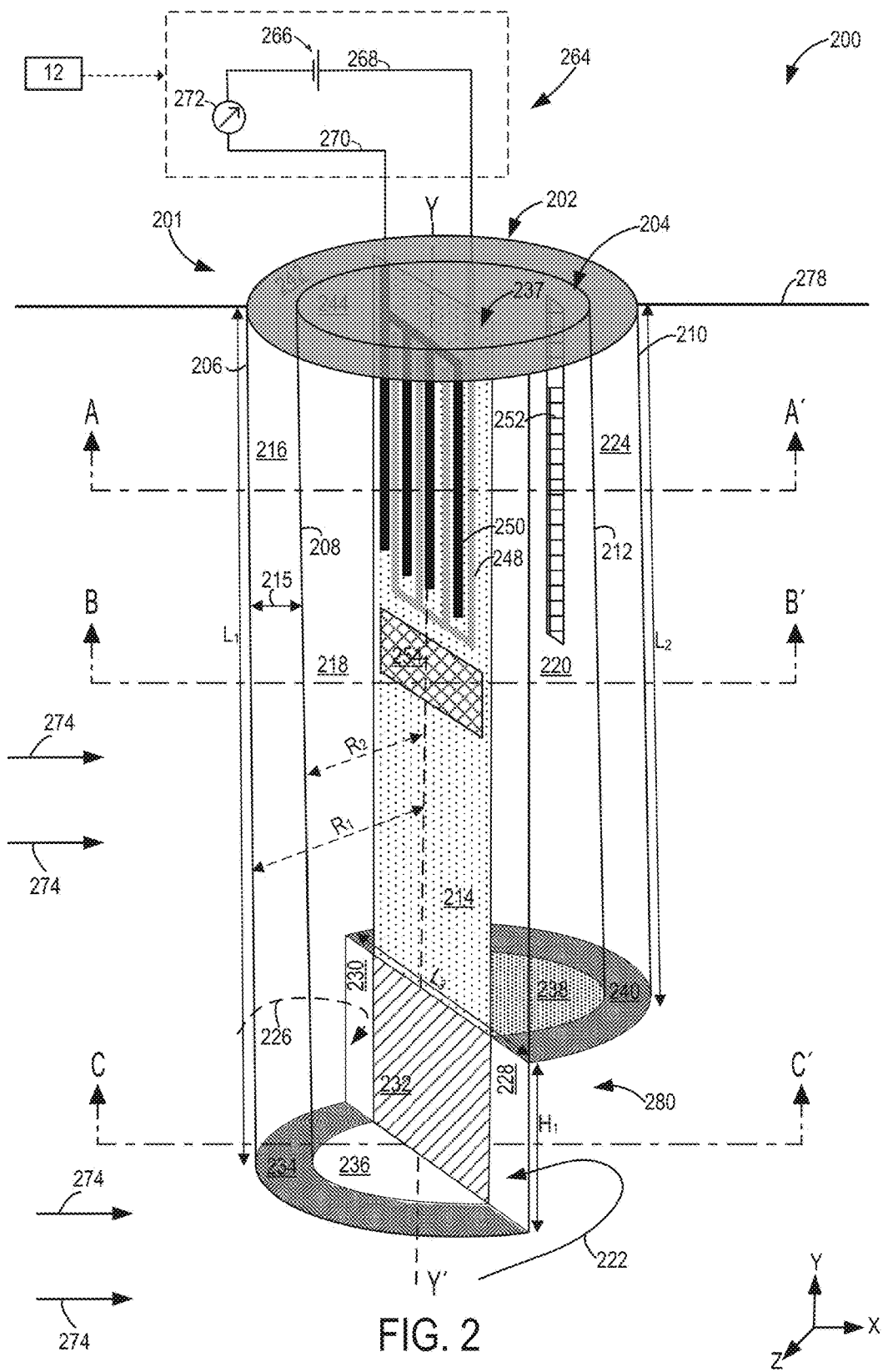
FIG. 2 shows a schematic diagram of the PM sensor assembly including an outer stepped tube, an inner stepped tube, and a plate including a sensor element.
Figure 4:
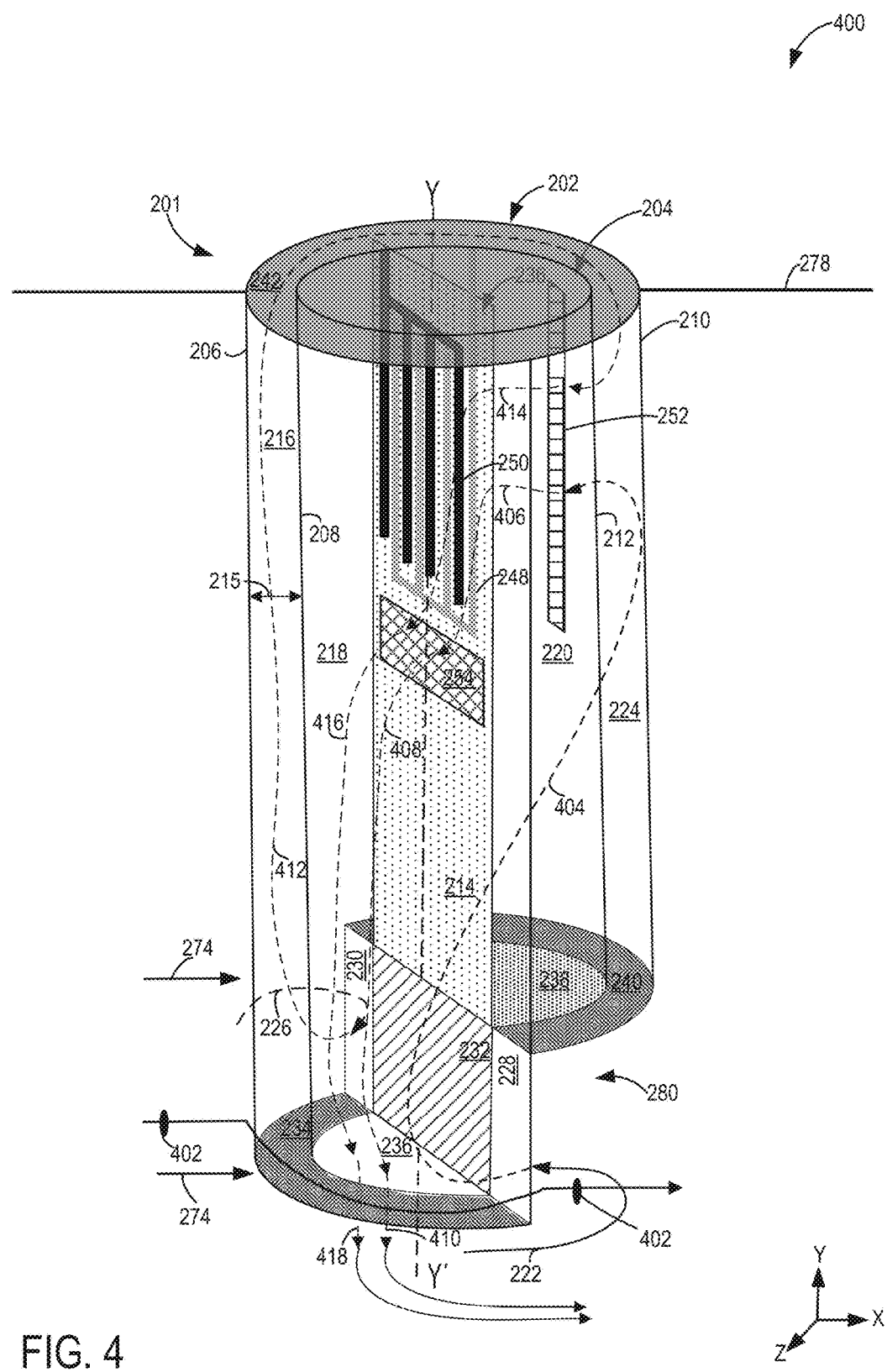
FIG. 4 shows a schematic diagram of the PM sensor assembly showing exhaust flowing into the PM sensor assembly via the step.

A PM sensor assembly may be placed in an exhaust passage of the engine system. The PM sensor assembly may include an outer stepped tube, an inner stepped tube positioned within the outer tube, and a plate including sensor elements positioned within the assembly, as shown in FIG. 2. As such, the outer and the inner tube may include a step formed as a result of an inherent asymmetry of the outer and inner tubes. For example, the outer and the inner tube may each include two semi-circular regions of unequal lengths. When the semi-circular regions of each of the outer and the inner tubes are coupled together, a difference in lengths of the regions may result in the step. Cross-sectional views of the inner and the outer tubes are shown in FIGS. 3A-3C. By including inlets in the step, exhaust flow in the exhaust passage may be directed into the PM sensor assembly via the inlets in a direction opposite to the direction of exhaust flow in the exhaust passage towards the sensor elements positioned within the assembly, as shown in FIG. 4. A controller may be configured to perform a control routine, such as an example routine of FIG. 5 to accumulate particulates in the exhaust on the sensor elements. Further, the controller may intermittently clean the PM sensor assembly (FIG. 6) to enable continued PM monitoring. Furthermore, the controller may be configured to perform a routine, such as an example routine of FIG. 7 to regenerate the exhaust particulate filter based on a time between PM sensor regenerations. An example of filter diagnostics is shown in FIG. 8. In this way, the functioning of the PM sensor to estimate the filtering capabilities of the DPF (and thereby to detect DPF leaks) may be increased.

FIG. 1 shows a schematic depiction of a vehicle system 6. The vehicle system 6 includes an engine system 8. The engine system 8 may include an engine 10 having a plurality of cylinders 30. Engine 10 includes an engine intake 23 and an engine exhaust 25. Engine intake 23 includes a throttle 62 fluidly coupled to the engine intake manifold 44 via an intake passage 42. The engine exhaust 25 includes an exhaust manifold 48 eventually leading to an exhaust passage 35 that routes exhaust gas to the atmosphere. Throttle 62 may be located in intake passage 42 downstream of a boosting device, such as a turbocharger (not shown), and upstream of an after-cooler (not shown). When included, the after-cooler may be configured to reduce the temperature of intake air compressed by the boosting device.

Engine exhaust 25 may include one or more emission control devices 70, which may be mounted in a close-coupled position in the exhaust. One or more emission control devices may include a three-way catalyst, lean NOx filter, SCR catalyst, etc. Engine exhaust 25 may also include diesel particulate filter (DPF) 102, which temporarily filters PMs from entering gases, positioned upstream of emission control device 70. In one example, as depicted, DPF 102 is a diesel particulate matter retaining system. DPF 102 may have a monolith structure made of, for example, cordierite or silicon carbide, with a plurality of channels inside for filtering particulate matter from diesel exhaust gas. Tailpipe exhaust gas that has been filtered of PM, following passage through DPF 102, may be measured in a PM sensor 106 and further processed in emission control device 70 and expelled to the atmosphere via exhaust passage 35. In the depicted example, PM sensor 106 is a resistive sensor that estimates the filtering efficiency of the DPF 102 based on a change in conductivity measured across the electrodes of the PM sensor. A schematic view 200 of the PM sensor 106 is shown at FIG. 2, as described in further detail below.

The vehicle system 6 may further include control system 14. Control system 14 is shown receiving information from a plurality of sensors 16 (various examples of which are described herein) and sending control signals to a plurality of actuators 81 (various examples of which are described herein). As one example, sensors 16 may include exhaust flow rate sensor 126 configured to measure a flow rate of exhaust gas through the exhaust passage 35, exhaust gas sensor (located in exhaust manifold 48), temperature sensor 128, pressure sensor 129 (located downstream of emission control device 70), and PM sensor 106. Other sensors such as additional pressure, temperature, air/fuel ratio, exhaust flow rate and composition sensors may be coupled to various locations in the vehicle system 6. As another example, the actuators may include fuel injectors 66, throttle 62, DPF valves that control filter regeneration (not shown), switch of electric circuit, etc. The control system 14 may include a controller 12. The controller 12 may be configured with computer readable instructions stored on non-transitory memory. The controller 12 receives signals from the various sensors of FIG. 1, processes the signals, and employs the various actuators of FIG. 1 to adjust engine operation based on the received signals and instructions stored on a memory of the controller. As an example, while operating the PM sensor to accumulate soot particulates, the controller send a control signal to an electric circuit to apply a voltage to the sensor electrodes of the PM sensor assembly to trap the charged particulates onto the surface of the sensor electrodes. As another example, during PM sensor regeneration, the controller may send a control signal to a regeneration circuit to close a switch in the regeneration circuit for a threshold time to apply a voltage to heating elements coupled to the sensor electrodes to heat the sensor electrodes. In this way, the sensor electrodes are heated to burn off soot particles deposited on the surface of the sensor electrodes. Example routines are described herein with reference to FIGS. 5-7.

Turning now to FIG. 2, a schematic view 200 of an example embodiment of a particulate matter (PM) sensor assembly 201 (such as PM sensor 106 of FIG. 1) is shown. The PM sensor assembly 201 may be configured to measure PM mass and/or concentration in the exhaust gas, and as such, may be coupled to an exhaust passage 278 (e.g., such as the exhaust passage 35 shown in FIG. 1), upstream or downstream of a diesel particulate filter (such as DPF 102 shown in FIG. 1).

In the schematic view 200, the PM sensor assembly 201 is disposed inside the exhaust passage 278 with exhaust gases flowing (along X-axis) from downstream of the diesel particulate filter towards an exhaust tailpipe, as indicated by arrows 274. The PM sensor assembly 201 includes an outer, stepped tube 202, an inner, stepped tube 204 positioned inside the outer tube 202. The PM sensor assembly 201 further includes a plate 214 having a sensor element 237 positioned within the inner tube 204. The outer tube 202 and the inner tube 204 may each be asymmetrical tubes. Together, the outer tube 202 and the inner tube 204 form an asymmetric protection tube of the PM sensor assembly 201, for example.

The outer tube 202 may be a hollow cylindrical tube of radius $R_1$ mounted to a top end of the exhaust passage 278 via sensor boss (not shown). The inner tube 204 may be a hollow cylindrical tube of radius $R_2$ positioned coaxially within the outer tube 202, and separated from the outer tube 202 by a space/gap 215. Herein, the inner tube 204 is smaller than the outer tube 202 (e.g., $R_2<R_1$), and the gap 215 between the outer tube 202 and the inner tube 204 is equal to a difference in the radii of the two tubes (e.g., $R_2-R_1$). As such, the inner tube 204 may be held to the outer tube 202 by screws (not shown) located along side surfaces of the outer tube 202, for example. The outer tube 202 and the inner tube 204 may share a common central axis Y-Y' that is perpendicular to the direction of exhaust flow (arrow 274) inside the exhaust passage 278. However, the inner tube 204 and the outer tube 202 may not be symmetrical.

For example, the outer tube 202 may include two semi-circular regions of unequal lengths forming the asymmetric stepped outer tube. Herein, the outer tube 202 includes a first semi-circular region or segment 206 of length $L_1$, fluidically coupled to a second semi-circular region or segment 210 of length $L_2$, wherein $L_1$ is greater than $L_2$. The first region 206 and the second region 210 include a common top surface 242. The difference ($L_1$–$L_2$) between the first and the second region gives rise to the asymmetry in the outer tube 202. The asymmetry in the outer tube 202 forms a step 280. As such, the longer first region 206 is positioned closer to the particulate filter positioned upstream of the PM sensor assembly 201, and further away from the exhaust tailpipe. Additionally, the shorter second region 210 is fluidically coupled to the first region 206 and positioned closer to the exhaust tailpipe, and further away from the particulate filter.

Similarly, the inner tube 204 may include two semi-circular regions of unequal lengths forming the asymmetrical stepped inner tube 204. Herein, the inner tube 204 includes a first semi-circular region or segment 208 of length $L_1$ coupled to a second semi-circular region or segment 212 of length $L_2$, wherein $L_1$ is greater than $L_2$. In one example, the length of first region 208 of the inner tube 204 is substantially equal to the length of the first region 206 of the outer tube 202. In another example, the length of first region 208 of the inner tube 204 may not be equal to the length of the first region 206 of the outer tube 202. Further, the first region 208 of the inner tube 204 is positioned within the first region 206 of the outer tube 202. Thus, the first region 208 of the inner tube 204 is closer to the particulate filter positioned upstream of the PM sensor assembly 201, and further away from the exhaust tailpipe. Likewise, the length of the second region 212 of the inner tube 204 is substantially equal to the length of the second region 210 of the outer tube 202. In an example embodiment, the length of the second region 212 of the inner tube 204 may not be equal to the length of the second region 210 of the outer tube 202. The second region 212 of the inner tube 204 may be positioned within the second region 210 of the outer tube 202. Similar to the outer tube 202, the difference in lengths of the first region 208 and the second region 212 of the inner tube 204 forms the step 280.

The inner tube 204 includes the plate 214 positioned therewithin. In one example, the plate 214 may be positioned centrally within the inner tube 204, and may further be configured to be an extension of the step 280. Thus, an edge of the plate 214 may be coupled to an edge of the step 280 such that the plate 214 is contiguous with the step 280. Herein, plate 214 may include a long axis that coincides with (is coaxial to) the central axis Y-Y'. The plate 214 separates the first region 208 and the second region 212 of the inner tube 204, for example.

The plate 214 is positioned within the inner tube 204 such that the plate 214 is orthogonal to the direction of exhaust flow (arrow 274) inside the exhaust passage 278. In addition, the plate 214 is positioned orthogonal to a long axis of the exhaust passage 278. The plate 214 divides the inner tube 204 into a first volume 218 and a second volume 220. Herein, the first volume 218 is the volume enclosed within the first region 208 of the inner tube 204. The second volume 220 is the volume enclosed within the second region 212 of the inner tube 204. The first volume 218 is greater than the second volume 220 (since $L_1$>$L_2$, for example).

Turning to FIG. 3A, a cross-sectional view 300 of the PM sensor assembly 201 in a plane along line A-A' of FIG. 2 is shown. Herein, a cross-section of the outer tube 202, the inner tube 204, and the plate 214 is shown. Briefly, the inner tube 204 is a smaller hollow cylindrical tube that is positioned inside the outer tube 202. In one example, the plate 214 is positioned centrally within the inner tube 204 such that the plate 214 divides the inner tube 204 into the first larger volume 218 and the second smaller volume 220. It may be appreciated that the first volume 218 of the inner tube 204 is fluidically separated from the second volume 220 of the inner tube 204 by the plate 214.

An axis Z-Z' in the view 300 may divide the outer tube 202 into two volumes; a first volume 216 and a second volume 224. Herein, the first volume 216 of the outer tube 202 may be the volume enclosed in the gap between the first region 206 of the outer tube 202 and the first region 208 of the inner tube 204. Likewise the second volume 224 may be the volume enclosed in the gap between the second region 210 of the outer tube 202 and the second region 212 of the inner tube 204. Similar to the inner tube 204, the first volume 216 of the outer tube 202 may be larger than the second volume 224 of the outer tube 202. Contrary to the inner tube 204, the first volume 216 of the outer tube 202 may be fluidically coupled to the second volume 224 of the outer tube 202. Together, the first volume 216 and the second volume 224 make up the volume enclosed in the gap between the inner and the outer tubes, for example. Thus, exhaust inside the first volume 216 enclosed within first region 206 of the outer tube 202 may spiral into the second volume 224. Herein, the second volume 224 is enclosed between the second region 210 of the outer tube 202 and the second region 212 of the inner tube 204. The exhaust inside the second volume 224 of the outer tube 202 may enter the second region 212 of the inner tube 204 via a slit 252. Herein, the slit 252 is formed on a surface of the second region 212 of the inner tube 204 such that exhaust gas flows from the second region 210 of the outer tube 202 into the second region 212 of the inner tube 204 in a direction opposite to exhaust flow in the exhaust passage. Thus, exhaust trapped within the gap between the outer and the inner tubes gets released into the inner tube 204 via the slit 252. Specifically, exhaust from the second volume 224 of the outer tube 202 flows into the second volume 220 of the inner tube via the slit 252 towards the plate 214, for example. The path of the exhaust gas within the PM sensor assembly will be described in greater detail in FIG. 4.

Herein, the plate 214 positioned within the inner tube 204 includes a sensor element 237 configured to accumulate soot particles in the exhaust entering the inner tube 204 via the slit 252. As such, the sensor element 237 includes electrodes 312 formed on a substrate 310. The substrate 310 is in face-sharing contact with the plate 214 and is further perpendicular to each of the direction of exhaust flow (arrow 274) in the exhaust passage, and a long axis of the exhaust passage. The substrate 310 of the sensor element 237 may be typically manufactured from highly electrically insulating materials. Possible electrically insulating materials may include oxides such as alumina, zirconia, yttria, lanthanum oxide, silica, and combinations comprising at least one of the foregoing, or any like material capable of inhibiting electrical communication and providing physical protection for the electrodes 312. Various designs for layout of the electrodes 312 is possible. An example layout of the electrodes 312 is shown in FIG. 2.

Returning to FIG. 2, a pair of interdigitated electrodes of the sensor element 237 is shown. Herein, a pair of planar interdigitated electrodes 250 and 248 may contain individual electrodes forming a "comb" structure indicated by black and grey lines in view 200. These electrodes may be typically manufactured from metals such as platinum, gold, osmium, rhodium, iridium, ruthenium, aluminum, titanium, zirconium, and the like, as well as, oxides, cements, alloys and combination comprising at least one of the foregoing metals. Each electrode of the interdigitated pair may be composed of the same or different material as the other electrode of the pair. For example, the electrode 248 may be composed of the same material as the electrode 250. In another example, electrode 248 and electrode 250 may be composed of different materials. The spacing between the comb "tines" of the two electrodes may typically be in the range from 10 micrometers to 100 micrometers with the linewidth of each individual "tine" being about the same value, although the latter is not necessary. The electrodes 248 and 250 may be connected via electrical connections to an electric circuit 264. The electrode 248 of the sensor element 237 is connected with connecting wire 268 to a positive terminal of a voltage source 266 of the electric circuit 264. Thus, the electrode 248 may be referred to as a positive electrode. Similarly, electrode 250 of the sensor element 237 is connected to a measurement device 272 via a connecting wire 270, and further connected to a negative terminal of the voltage source 266 of the electric circuit 264. Thus, the electrode 250 may be referred to as a negative electrode. The interconnecting wires 268 and 270, the voltage source 266 and the measurement device 272 are part of the electric circuit 264 and are housed outside the exhaust passage 278 (as one example, <1 meter away). Further, the voltage source 266 and the measurement device 272 of the electric circuit 64 may be controlled by a controller, such as controller 12 of FIG. 1, so that particulate matter collected at the PM sensor may be used for diagnosing leaks in the DPF, for example. As such, the measurement device 272 may be any device capable of reading a resistance (or current) change across the electrodes, such as a voltmeter (or an ammeter). As PM or soot particles get deposited between the electrodes 248 and 250, the current measured between the electrodes 248 and 250 may start to increase, which is measured by the measurement device 272. The controller 12 may be able to determine the current and infer a corresponding PM or soot load on the planar electrodes 248 and 250 of the sensor element 237 of the PM sensor assembly 201. By monitoring the load on the sensor element 237, the exhaust soot load downstream of the DPF may be determined, and thereby used to diagnose and monitor the health and functioning of the DPF.

The sensor element 237 additionally includes a heating element (not shown) that is integrated into the sensor substrate. In alternate embodiments, the sensor element 237 may not include a heating element. The heating element may comprise, but is not limited to, a temperature sensor, and a heater. Possible materials for the heater and the temperature sensor forming the heating element may include platinum, gold, palladium, and the like; and alloys, oxides, and combinations comprising at least one of the foregoing materials, with platinum/alumina, platinum/palladium, platinum, and palladium. The heating element may be used for regenerating the sensor element 237. Specifically, during conditions when the particulate matter load or soot load of the sensor element 237 is higher than a threshold, the heating element may be operated to burn accumulated soot particles from the surface of sensor. During PM sensor regeneration, the controller 12 may send a control signal to a regeneration circuit to apply a certain voltage to the heating element. For example, the regeneration circuit may be part of the electric circuit 264 and may include an additional voltage source, a switch and connecting wires connecting the voltage source to the heating element. As an example, the controller may send a control signal to close the switch in the regeneration circuit for a threshold time to apply the voltage to the heating element in order to raise the temperature of the heating element. Subsequently, when the sensor electrodes are sufficiently clean, the controller may send a control signal to open the switch in the regeneration circuit to stop heating the heating element. By intermittently regenerating the sensor element 237, it may be returned to a condition (e.g., unloaded or only partially loaded condition) more suitable for collecting exhaust soot. In addition, accurate information pertaining to the exhaust soot level may be inferred from the sensor regeneration and this information may be used by the controller for diagnosing leaks in the particulate filter.

As such contaminants such as large particulates and water droplets in the exhaust may impinge on the sensor electrodes leading to abrupt changes in the sensor output. This may lead to fluctuations in sensor sensitivity and hence the particulate filter leak monitoring by the sensor may no longer be reliable. The inventors have recognized that it may be possible to filter out larger particulates and water droplets at the step 280 formed in the inner and outer tube by leveraging the higher resistance of the larger particulates to a reversal in flow direction.

As such, the sensor element 237 may be formed on the plate 214, closer to the top of the exhaust passage 278 than the step 280. In addition, the plate may include a slit 254 positioned below the sensor element 237. Herein, the slit 254 is between the sensor element 237 and the step 280, and closer to the sensor element 237 than the step 280. Turning to FIG. 3B, a cross-sectional view 325 of the PM sensor assembly 201 in a plane along line B-B' of FIG. 2 is shown. Herein, a cross-section of the outer tube 202, the inner tube 204, and the plate 214 including the slit 254 is shown. In general, the plate 214 separates the first volume 218 of the first region 208 from the second volume 220 enclosed within the second region 212 of the inner tube 204 such that there may be no fluidic communication between the two volumes at the plate. However, at the slit 254, the second volume 220 is fluidically coupled to the first volume 218 of the inner tube 204. Thus, exhaust that has entered the second volume 220 (via slit 252, as described in FIG. 3A) for example, may be able to flow into the first volume 218 only via the slit 254.

The slit 254 formed on the plate 214 is positioned along Z-Z', which is orthogonal to the central axis Y-Y'. Further, the slit 254 is orthogonal to the direction of exhaust flow (arrow 274) in the exhaust passage. Herein, the direction of flow of exhaust from the second volume 220 into the first volume 218 of the inner tube 204 is opposite to the direction of exhaust flow (arrow 274) in the exhaust passage. In this way, once soot particulates are deposited on the sensor electrodes formed on the plate 214, the exhaust may get released via the slit 254 into the first volume 218 enclosed within the inner tube 204. As such, exhaust may be released from the first volume 218 into the exhaust passage via a bottom surface of the inner tube 204 as explained below.

Returning to FIG. 2, the inner tube 204 includes the first region 208 extending from a top surface 244 of the inner tube 204 to a first bottom surface 236 of the inner tube. Herein, the first region 208 of the inner tube 204 enclosed the first volume 218, for example. The first bottom surface 236 may not be sealed, therefore allowing the exhaust inside the first region 208 of the inner tube 204 to get released into the exhaust passage via the first bottom surface 236. As such, the exhaust may exit in a direction orthogonal to the direction of exhaust flow (arrow 274) in the exhaust passage 278. However, exhaust may not enter the PM sensor assembly 201 via the surface 236. Exhaust enters the PM sensor assembly 201 solely via the step 280 as described below.

The outer tube 202 includes the first region 206 extending up to a length $L_1$ from a top surface 242 to a first bottom surface 234 of the outer tube 202. The second region 210 of the outer tube 202 is of length $L_2$ extending from the top surface 242 to a second bottom surface 240. In addition, the first bottom surface 234 is not coplanar with the second bottom surface 240 of the outer tube 202. The difference in the lengths of the first region 206 and the second region 210 of the outer tube 202 forms the step 280 of height $H_1$ which equals $L_1-L_2$. Thus, the first bottom surface 234 of the outer tube 202 is separated from the second bottom surface 240 of the outer tube 202 by a distance that is equal to the height $H_1$ of the step 280.

Herein, the first bottom surface 234 and the second bottom surface 240 of the outer tube 202 are annular regions. The annular region includes a width that is substantially equal to the gap 215 between the outer tube 202 and the inner tube 204. Further, the first bottom surface 234 and the second bottom surface 240 of the outer tube 202 are sealed. Thus, exhaust gas may neither enter nor exit the PM sensor assembly 201 via each of the first and second bottom surfaces of the outer tube 202.

Similar to the outer tube 202, the inner tube 204 includes two regions of different lengths. The inner tube 204 includes the first region 208 extending up to a length $L_1$ from a top surface 244 to the first bottom surface 236 of the inner tube 204. The second region 212 of the inner tube 204 is of length $L_2$ extending from the top surface 244 to a second bottom surface 238. In addition, the first bottom surface 236 is not coplanar with the second bottom surface 238 of the inner tube 204. The difference in the lengths of the first region 208 and the second region 212 of the inner tube 204 forms the step 280 of height $H_1$ which equals $L_1-L_2$. Thus, the first bottom surface 236 of the inner tube 204 is separated from the second bottom surface 238 of the inner tube 204 by a distance that is equal to the height $H_1$ of the step 280.

In summary, the first bottom surface 236 is not coplanar with the second bottom surface 238 of the inner tube 204. However, the first bottom surface 236 of the inner tube 204 is coplanar with the first bottom surface 234 of the outer tube 202. Likewise, the second bottom surface 238 of the inner tube 204 is coplanar with the second bottom surface 240 of the outer tube 202. Thus, the set of coplanar first bottom surfaces 234 and 236 of the outer and inner tubes are not coplanar with the set of second bottom surfaces 238 and 240 of the outer and inner tubes.

Further, the first bottom surface 236 and the second bottom surface 238 of the inner tube 204 may each be a semi-circular region of radius $R_2$. The second bottom surface 238 may be sealed so that exhaust gas neither enters nor exits the PM sensor assembly 201 via the second bottom surface 238 of the inner tube 204. As described earlier, the first bottom surface 236 of the inner tube 204 may not be sealed. Thus, exhaust gas inside the PM sensor assembly 201 may exit the assembly via the first bottom surface 236 of the inner tube 204. As such, the exhaust may be released from the PM sensor assembly 201 via the first bottom surface 236 of the inner tube 204 in a direction orthogonal to the direction of exhaust flow (arrow 274) in the exhaust passage 278.

Turning to FIG. 3C, a cross-sectional view 350 of the PM sensor assembly 201 in a plane along line C-C' of FIG. 2 is shown. Herein, a cross-section of the first bottom surfaces of each of the inner tube 204 and outer tube 202, and the step 280 is shown. Briefly, the first bottom surface 236 of the inner tube 204 has semi-circular cross-section of radius $R_2$, and is coplanar with the first bottom surface 234 of the outer tube 202. The first bottom surface 234 of the outer tube 202 is an annulus (or ring) with a width equal to the difference in the radius of the outer and inner tubes. As such, the first bottom surface 234 of the outer tube 202 and the first bottom surface 236 of the inner tube 204 may each be coupled to a bottom end of the step 280. A top end of the step 280 may be coupled to the second bottom surface of the inner and the outer tubes. Herein, a length $L_3$ of the step 280 is substantially equal to the radius R1 of the outer tube 202. As described earlier, exhaust inside the PM sensor assembly exits via the first bottom surface 236 of the inner tube 204. In the view 350, exhaust may flow out of the assembly along the Y-axis (and into the plane of the paper, for example), which is orthogonal to the direction of flow of exhaust (arrow 274) in the exhaust passage (e.g., exhaust flows along X-axis)

However, exhaust may enter the PM sensor assembly 201 solely via the step 280. The inventors have recognized that the step 280 formed as a result of asymmetry in each of the outer and inner tube may be advantageously used to block contaminants from entering the PM sensor assembly 201, for example. Further, the step 280 may be additionally included inlets to direct exhaust gas into the PM sensor assembly 201 as described below.

Returning to FIG. 2, the step 280 may be formed along a surface perpendicular to the direction of exhaust flow (arrow 274) in the exhaust passage. In addition, the step 280 may be orthogonal to the exhaust passage 278. Herein, the step 280 includes a sealed surface 232 and two inlets 228 and 230 positioned on either side of the sealed surface 232.

Inlets 228 and 230 may be formed on opposite sides of the step 280 such that exhaust gas may be directed into the PM sensor assembly 201 via the inlets in a direction opposite to the direction of exhaust flow (arrow 274) in the exhaust passage 278. In addition, the inlets 228 and 230 may direct exhaust flow in to the gap 215 between the inner and outer tubes, for example. In one example embodiment, the inlets 228 and 230 may be rectangular openings of a height that is substantially equal to the height $H_1$ ($L_1-L_2$, for example) of the step 280. Herein, a width of the inlets 228 and 230 may be equal to the gap 215 (e.g., $R_2-R_1$) between the outer and the inner tube of the PM sensor assembly 201. The sealed surface 232 of the step 280 may be sandwiched on either side by the inlets 228 and 230. As such, a width of the sealed surface 232 is equal to the radius $R_2$ of the inner tube 204. Further, a height of the sealed surface is equal to the height $H_1$ of the step 280, and additionally equal to the height of the inlets 228 and 230.

The sealed surface 232 blocks exhaust flow into the PM sensor assembly 201. However, the inlets 228 and 230 allow exhaust in the exhaust passage 278 to enter the PM sensor assembly 201.

Thus, an example particulate matter sensor assembly includes an outer stepped tube having a first semi-circular region and a second semi-circular region, the first region being longer than the second region, an inner stepped tube coaxial to the outer stepped tube having a third semi-circular region and a fourth semi-circular region, the third region being longer than the fourth region, and a plate positioned inside the inner stepped tube having a sensor element.

Additionally or alternatively, the inner stepped tube may be positioned coaxially within the outer stepped tube and may be separated from the outer stepped tube by a gap, and wherein a top surface of the inner stepped is coplanar with a top surface of the outer stepped tube. Additionally or alternatively, the first region may include a first, sealed bottom surface and the second region includes a second, sealed bottom surface, the first bottom surface not coplanar with the second bottom surface. Additionally or alternatively, the third region may include a third, unsealed bottom surface and the fourth region includes a fourth, sealed bottom surface, the third bottom surface not coplanar with the fourth bottom surface. Additionally or alternatively, the first bottom surface may be coplanar with the third bottom surface and the second bottom surface may be coplanar with the fourth bottom surface. Additionally or alternatively, the third region may be positioned coaxially within the first region, each of the first region and the third region may extend to a first distance in an exhaust pipe. Additionally or alternatively, the fourth region may be positioned coaxially within the second region, each of the second region and the fourth region extending to a second distance in the exhaust pipe. Additionally or alternatively, a difference between the first distance and the second distance may form a step, a height of the step being substantially equal to the difference. Additionally or alternatively, a length of the step may be substantially equal to a diameter of the first region and the second region. Additionally or alternatively, the step may include inlets that allow exhaust gas flowing in the exhaust pipe to reverse flow direction and enter via the inlets and into the annular space between the inner stepped tube and the outer stepped tube. Additionally or alternatively, the third region may include a first slit for flowing the exhaust gas from the annular space into a first space formed by the plate and the fourth region and towards the sensor element positioned coaxially within the inner tube. Additionally or alternatively, the plate includes a second slit for directing the exhaust gas from the first space into a second space formed by the plate and the third region, and further towards an exit in the third bottom surface.

As such, the exhaust may enter the inlets 228 and 230 by reversing the direction of flow as shown in FIG. 4. Turning to FIG. 4, a schematic view 400 shows exhaust flow through the PM sensor assembly 201. Specifically, view 400 depicts exhaust flowing into the PM sensor assembly 201 via the inlets 228 and 230 formed on the step 280. As such, the step 280 is formed as a result of coupling asymmetrical inner and outer tubes as explained earlier.

Exhaust gas flows along the X-axis inside the exhaust passage 278 as indicated by the arrow 274 from an upstream particulate filter towards PM sensor assembly 201, for example. Exhaust gas may include contaminants 402 such as larger particulates and water droplets. The inlets 228 and 230 formed on the step 280 allow exhaust to enter the assembly in a direction indicated by arrows 222 and 226, opposite to the direction of exhaust flow (274) in the exhaust passage 278. The inlets 228 and 230 are on a side of the PM sensor assembly 201 that is closer to an end of the exhaust tailpipe and further away from the particulate filter upstream of the PM sensor assembly 201. As exhaust flows in the exhaust passage 278, in a region around the inlets 228 and 230, static pressure gradients are created. Herein, a higher static pressure exits at and near the inlets 228 and 230 than at regions away from the inlets 228 and 230. As a result, exhaust gas gets steered into the PM sensor assembly 201 via the inlets 228 and 230. The portion of the exhaust gas entering via the inlets 228 and 230 undergoes a reversal in flow direction prior to entering the sensor. The contaminants 402 may be large in size and thus may not be affected by the static pressure gradient generated at and near the inlets 228 and 230. The contaminants 402 may continue to flow past the PM sensor assembly 201 in the exhaust passage, and be expelled out of the exhaust pipe. Thereby, the sensor element 237 of the PM sensor assembly 201 positioned within the inner tube 204 may be protected from impingement of water droplets and larger particulates. In this way, by creating a static pressure gradient at the inlets and steering the exhaust in a reverse direction into the PM sensor assembly via the inlets, it may be possible to filter out larger particulates and water droplets thereby reducing the amount of contaminants entering the PM sensor assembly 201. Further, inlets on the step of the PM sensor assembly may be sized, shaped, and positioned to generate uniform flow of exhaust gases onto the sensor surface. Thus, the sensor electrodes may be protected from impingement of water droplets and larger particulates and the PM sensor may be made more reliable. Overall, the functioning of the PM sensor to estimate the filtering capabilities of the DPF (and thereby to detect DPF leaks) may be increased and exhaust emissions compliance may be boosted as particulates in the exhaust may be detected more accurately and reliably.

The portion of the exhaust entering the PM sensor assembly 201 via the inlet 228 of the step 280 flows into the gap 215 between the outer tube 202 and the inner tube 204. Specifically, the portion of the exhaust entering via the inlet 228 (arrow 222) due to a pressure gradient as previously described, enters the PM sensor assembly 201 in a direction opposite to the direction of exhaust flow (arrow 274) in the exhaust passage 278. Similarly, the portion of the exhaust entering the assembly via the inlet 230 of the step 280 as indicated by arrow 226 enters in a direction opposite to direction of exhaust flow 274.

As an example, the portion of the exhaust flows into the first volume 216 and spirals in the gap 215 and flows into the second volume 224 of the outer tube 202. Herein, the first volume 216 is enclosed between the first semi-circular region 206 of the outer tube 202 and the first semi-circular region 208 of the inner tube 204. Likewise, the second volume 224 is enclosed between the second region 210 of the outer tube 202 and the second region 212 of the inner tube 204. It may be noted that the first volume 216 is fluidically coupled to the second volume 224. Further, each of the first bottom surface 234, the second bottom surface 240, and the top surface 242 are sealed surfaces. Therefore, the portion of the exhaust may swirl in the gap between the inner and the outer tubes and may be trapped within the gap as indicated by arrows 404 and 412. As such, the spiraling or swirling action of the exhaust inside the gap may decrease the flow rate of the exhaust.

However, the second region 212 of the inner tube 204 includes a slit 252. In one example, the slit 252 may be configured as a rectangular cutout with a long axis parallel to the central axis Y-Y'. As such, a height of the slit 252 may be larger than a length of the slit 252. Various other geometries of the slit 252 may be possible without deviating from the scope of the disclosure. Other example geometries include apertures, holes, and the like.

As such, the slit 252 allows the portion of the exhaust in the second volume 224 of the outer tube 202 to enter the second volume 220. Herein, the second volume 220 includes volume enclosed between the second region 212 of the inner tube 204 and the plate 214 positioned within the inner tube 204. The direction of exhaust flow is indicated by arrows 406 and 414. The portion of the exhaust entering the second volume 220 flows in a direction opposite to direction of exhaust flow (arrow 274) in the exhaust passage 278. Further, the portion of exhaust flows through the slit 252 in a direction parallel to the flow of exhaust entering the PM sensor assembly 201 via the inlets 228 and 230 of the step. As such, the exhaust flowing into the second volume 220 is directed towards the plate 214 as indicated by arrows 406 and 414. Specifically, the exhaust is directed towards the sensor element 237 formed on the plate 214. As shown in FIG. 2, the sensor element 237 includes a pair of planar interdigitated electrodes 250 and 248 configured to accumulate soot particles in the exhaust across the electrodes. Thus, soot particles in the exhaust within the second volume 220 get accumulated across the electrodes 248 and 250 of the sensor element 237.

In one example, a length of the slit 252 may be substantially equal to a length of the sensor element 237 formed on the plate 214. Thus, the sensor element 237 may experience a more uniform soot deposition through a direct flow impingement on the surface of the electrodes.

The plate 214 includes a slit 254 positioned below the sensor element 237. As an example, the slit 254 may be configured as a rectangular cutout with a long axis orthogonal to the central axis Y-Y'. Herein, the long axis of the slit 254 is orthogonal to the long axis of the slit 252. As an example, a length of the slit 254 may be larger than a height of the slit 254. Various other geometries of the slit 254 may be possible without deviating from the scope of the disclosure. Other example geometries include apertures, holes, and the like.

The slit 254 may be configured to direct exhaust gas from the second volume 220 into the first volume 218 of the inner tube (as indicated by arrows 408 and 416). For the most part, the first volume 218 is separated from the second volume 220 by the plate 214. However, the slit 254 formed on the plate 214 allows the first volume 218 to be fluidically coupled to the second volume 220. Thus, exhaust gas flows from the second volume 220 into the first volume 218 via the slit 254 in a direction opposite (as indicated by arrows 408 and 416) to the direction of exhaust flow (arrow 274) in the exhaust passage 278.

Exhaust inside the first volume 218 then gets released into the exhaust passage via the first bottom surface 236 of the inner tube 204. As described earlier, the first bottom surface 236 of the inner tube 204 is not sealed. Thus, exhaust gets released into the exhaust passage 278 via the first bottom surface 236 in a direction as indicated by arrows 418 and 410. Herein, the exhaust exits the PM sensor assembly 201 via a bottom surface of the inner tube 204 in a direction orthogonal to the direction of exhaust flow (arrow 274) inside the exhaust passage 278. In addition, the exhaust enters the PM sensor assembly 201 and exits the PM sensor assembly in orthogonal directions.

In this way, the PM sensor assembly may be configured with a step structure formed using asymmetrical inner and outer tubes. In addition, the step resulting from the asymmetry in the inner and the outer tubes may be configured to direct exhaust in the exhaust passage in a direction opposite to the direction of exhaust flow in the exhaust passage. As such, larger particulates in the exhaust may not be able to reverse the flow direction and enter the PM sensor assembly via the step. Thus, the step serves to block the larger particulates in the exhaust flow from impinging on the sensor element formed on the plate positioned within the assembly, thereby reducing sensor sensitivity fluctuations due to large particulates depositing on the sensor element.

As described earlier, the stepped assembly may be formed as a result of coupling semi-circular regions of unequal length. As another example, the stepped assembly may be generated by forming cutouts on hollow cylindrical tubes. To elucidate further, the outer stepped tube may be manufactured from an outer cylindrical hollow tube of radius R and of length L (e.g., R may be the radius $R_1$ of the outer tube 202 and length L may be length $L_1$ of outer tube 202 of FIG. 2) with a section cutout at an end of the tube. Herein, the section that is cutout may be a segment of length $L_4$, and radius $R_1$ cut from the outer tube at a length l (e.g., l may be the length $L_2$ of the second region 210 of outer tube 202 of FIG. 2) from a top of the outer tube. As such, $L_4$ is equal to $L_1$–$L_2$. Likewise, the inner stepped tube may be manufactured from a cylindrical hollow tube of radius r (wherein r<R) with a section cutout at an end of the tube (e.g., r may be the radius $R_2$ of the inner tube 204 of FIG. 2, for example). Herein, the section that is cutout may be a segment of length $L_4$, and radius r cut from the inner tube at a length l from a top of the inner tube. As such, $L_4$ is equal to L–l (and further equal to $L_1$–$L_2$, for example) The protection tube of the PM sensor assembly may be formed by arranging the smaller inner tube centrally within the larger outer tube and held to the outer tube with screws. As such, the top surface of the inner tube may be flush with the top surface of the outer tube. Further, the cutout section of the inner tube may be positioned within the cutout section of the outer tube. Herein, the cutout sections of each of the inner and the outer tube results in a step. As described earlier, the step may be configured to block larger particulates and further guide the exhaust into the PM sensor assembly to ensure a more uniform soot accumulation on the sensor element positioned inside the assembly.

Thus an example system includes a particulate matter (PM) sensor located downstream of a particulate filter in an exhaust passage, the PM sensor having an asymmetric protection tube including a step wherein the asymmetric protection tube includes a first segment coupled to a second segment, the first segment being longer than the second segment, and further wherein a difference in lengths between the first segment and the second segment generates the step. As an example, the first regions of the inner and the outer tubes together may form a first segment. Similarly, the second region of the inner and the outer tubes may form a second segment. Additionally or alternatively, the first segment may include a first volume and a second volume, and wherein the second segment includes a third volume and a fourth volume, the first volume being fluidically coupled to the third volume. Additionally or alternatively, the system may include a first inlet on the step directing exhaust in the exhaust passage into the first volume and subsequently into the third volume, a second inlet steering the exhaust gas from the third volume into the fourth volume, the fourth volume including sensor elements positioned on a plate, the plate separating the third volume and the second volume, a third inlet on the plate flowing the exhaust gas from the fourth volume into the second volume, and an outlet on the first segment directing the exhaust gas from the second volume into the exhaust passage. Additionally or alternatively, the system further comprises a controller with computer readable instructions stored on non-transitory memory for: accumulating particulates in the exhaust on the sensor elements, determining a load on the PM sensor based on a current generated between the sensor elements, and responsive to the load being higher than a threshold, regenerate the PM sensor (as described in FIGS. 5-6).

FIGS. 2-4 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space therebetween and no other components may be referred to as such, in at least one example. FIGS. 2-4 are shown drawn to scale, although other relative dimensions may be used.

Figure 5:
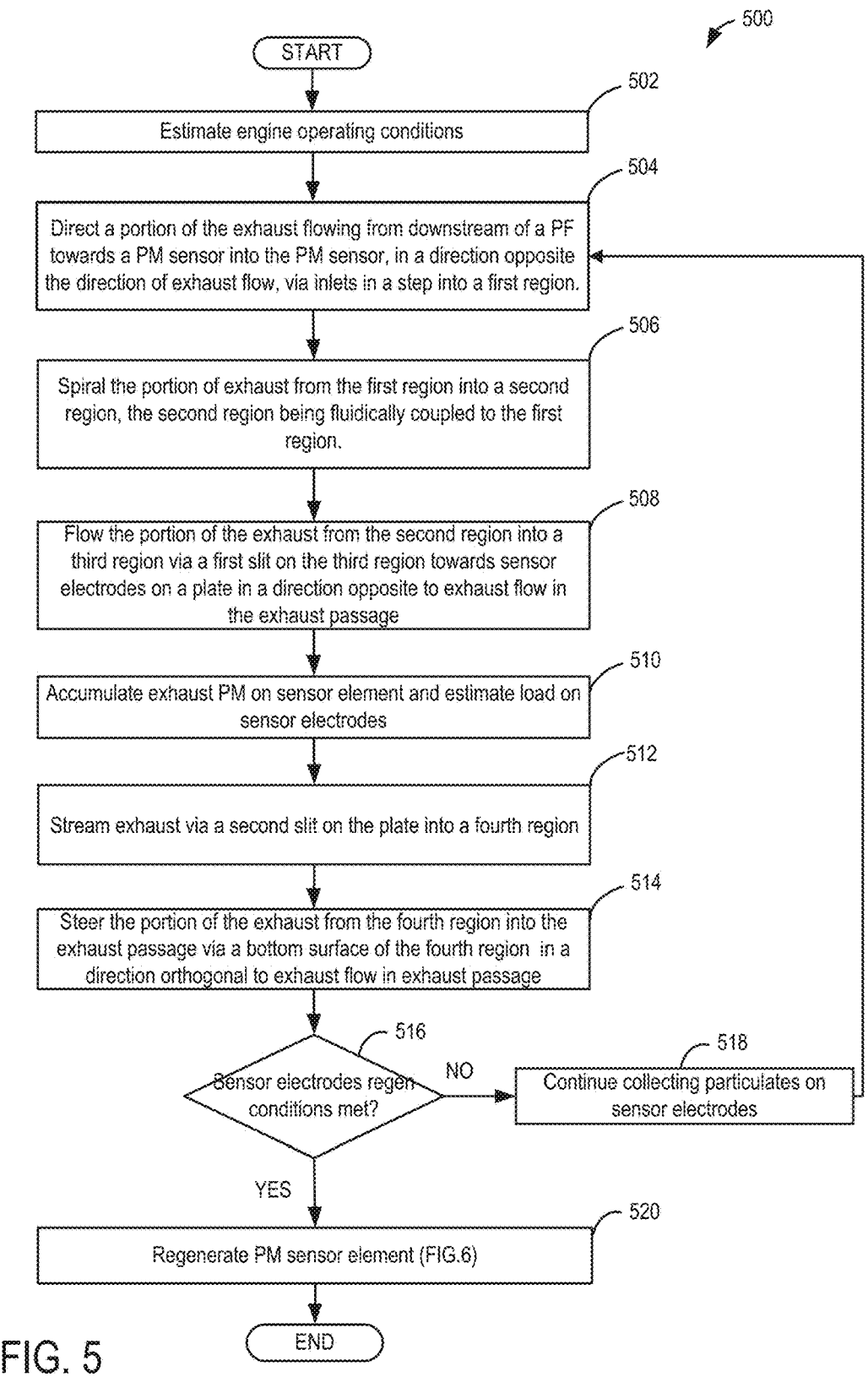
FIG. 5 shows a flow chart depicting an example method for accumulating particulates in the exhaust flow across the sensor element formed on the plate and positioned within the inner tube of the PM sensor assembly.

Turning now to FIG. 5, a method 500 for accumulating particulates in the exhaust flow across sensor electrodes positioned within the PM sensor (such as a PM sensor 106 shown at FIG. 1, and/or PM sensor assembly 201 of FIG. 2, for example) is shown. Specifically, the particulates in the exhaust flow may be accumulated across sensor electrodes formed on a plate and positioned within an asymmetrical protection tube of the PM sensor. Herein, the asymmetrical protection tube may include an inner asymmetrical tube positioned within an outer asymmetrical tube. As such, the inner and the outer tubes may include unequal segments which when coupled together result in a stepped tube assembly.

Instructions for carrying out method 500 and the rest of the methods 600 and 700 included herein may be executed by a controller based on instructions stored on a memory of the controller and in conjunction with signals received from sensors of the engine system, such as the sensors described above with reference to FIG. 1. The controller may employ engine actuators of the engine system to adjust engine operation, according to the methods described below.

At 502, method 500 includes determining and/or estimating engine operating conditions. Engine operating conditions determined may include, for example, engine speed, exhaust flow rate, engine temperature, exhaust air-fuel ratio, exhaust temperature, duration (or distance) elapsed since a last regeneration of the DPF, PM load on PM sensor, boost level, ambient conditions such as barometric pressure and ambient temperature, etc.

Method 500 proceeds to 504 where a portion of exhaust flowing from downstream of a particulate filter (such as DPF 102 of FIG. 1) is directed into a PM sensor via inlets formed on a step of the PM sensor. Herein, the portion of the exhaust is directed into a first region of the PM sensor. As such, the PM sensor includes an inner asymmetrical tube positioned within an outer asymmetrical tube and further separated from the outer tube by a gap. The first region is contained within the outer tube, and not within the inner tube. As an example, the outer tube may include the first region fluidically coupled to a second region. The first region may be a semi-circular region or segment of length $L_1$. Likewise, the second region may be a semi-circular region or segment of length $L_2$. Herein, $L_1$ is greater than $L_2$, resulting in the asymmetrical stepped form of the outer tube, for example. Similarly, the inner tube may include a third semi-circular region or segment coupled to a fourth semi-circular region or segment. Herein, the third region may be longer than the fourth region thereby forming the inner stepped tube. As described earlier, the inner and the outer tubes may be coupled together to form a step in the PM sensor. In addition, the step includes inlets configured to direct exhaust in a direction opposite to the direction of exhaust flow inside an exhaust passage. Specifically, a portion of the exhaust reverses the direction of flow in order to enter the PM sensor via the inlets of the step due to pressure gradients formed at and near the inlets of the step. A higher static pressure is created in and around the inlets in the step. As a result, a larger portion of the exhaust flows into the PM sensor via the inlets of the step. In addition, larger particulates and water droplets in the exhaust remain unaffected by the higher static pressure. Thus, the larger particulates and water droplets do not enter the PM sensor via the inlet, thereby reducing sensor errors due to these particulates depositing on the sensitive electrode surface, for example. It may be appreciated that the inlets of the step guide the portion of the exhaust into the first region, and not to any of the second, third, and fourth regions, for example.

As such, the portion of the exhaust enters into the first region of the PM sensor via the inlets of the step at 504. Next, method 500 proceeds to 506. At 506, method 500 includes spiraling the portion of the exhaust from the first region into the second region of the outer tube. For example, the first region is fluidically coupled to the second region. Thus, exhaust inside the first region swirls inside the gap formed between the outer and the inner tubes, and gets directed towards the second region of the outer tube.

Method 500 proceeds to 508. At 508, method 500 includes flowing the portion of the exhaust into a third region of the inner tube. Herein, the third regions includes a first slit formed on the surface such that the portion of the exhaust flowing from the second region into the third region flows in a direction opposite to the flow of exhaust in the exhaust passage. The first slit includes a first longer axis that is orthogonal to the direction of exhaust flow inside the exhaust passage, for example.

In addition, flowing of the exhaust into the third region via the first slit includes flowing the exhaust towards sensor electrodes formed on a plate positioned inside the inner tube. As such, the plate includes the sensor electrodes. As described earlier, the sensor electrodes include interdigitated positive and negative electrodes formed on a substrate that is coupled to the plate and is positioned facing towards the first slit, for example. Method 500 then proceeds to 510.

At 510, particulates in the portion of the exhaust streaming inside the third region are retained/accumulated between the sensor electrodes. The positive electrodes are connected to the positive terminal of a voltage supply and the negative electrodes are connected to a measurement device and then to the negative terminal of the voltage supply. When the controller applies a voltage to the sensor electrodes, particulates inside the third region may experience a strong electric field, enabling them to be accumulated between the electrodes. In addition, a load on the sensor electrodes is estimated based on a current generated in the sensor electrodes. When particulates accumulate on the surface of the sensor electrodes, the resistance of the electrodes starts decreasing and a current measured by the measurement device starts to increase. The controller may be able to deduce a load on the sensor electrodes based on the current measured across the electrodes. Method 500 then proceeds to 512.

At 512, method 500 includes streaming the portion of the exhaust from the third region into the fourth region via a second slit formed on the plate. Herein, the plate separates the third region and the fourth region. In addition, the plate includes the second slit positioned below the sensor electrodes through which the portion of the exhaust enters the fourth region, for example. As such, the second slit includes a second longer axis that is orthogonal to the direction of exhaust flow in the exhaust passage. In one example, the second axis of the second slit formed on the plate is orthogonal to the first axis of the first slit on the third region, for example. Method 500 then proceeds to 514.

At 514, method 500 includes steering the portion of the exhaust from the fourth region into the exhaust passage via a bottom surface of the fourth region. As such, the direction at which the exhaust exits the PM sensor is orthogonal to the direction of exhaust flow in the exhaust passage, for example. As described earlier, the bottom surface of each of the first, second, and third regions are sealed. The bottom surface of the fourth region is not sealed, and thereby allows the exhaust to get released into the exhaust passage via the bottom surface of the fourth region. Method 500 then proceeds to 516.

At 516, method 500 includes determining if the sensor electrode regeneration conditions are met. Specifically, when the soot load on the PM sensor is greater than the threshold, or when a resistance of the PM sensor (adjusted for temperature) drops to a threshold resistance, or when a current of the PM sensor is greater than a threshold current, PM sensor regeneration conditions may be considered met. In some examples, if a threshold time has elapsed since an immediately previous sensor regeneration, regeneration condition may be considered met. The PM sensor may require regeneration to enable further PM detection.

Figure 6:
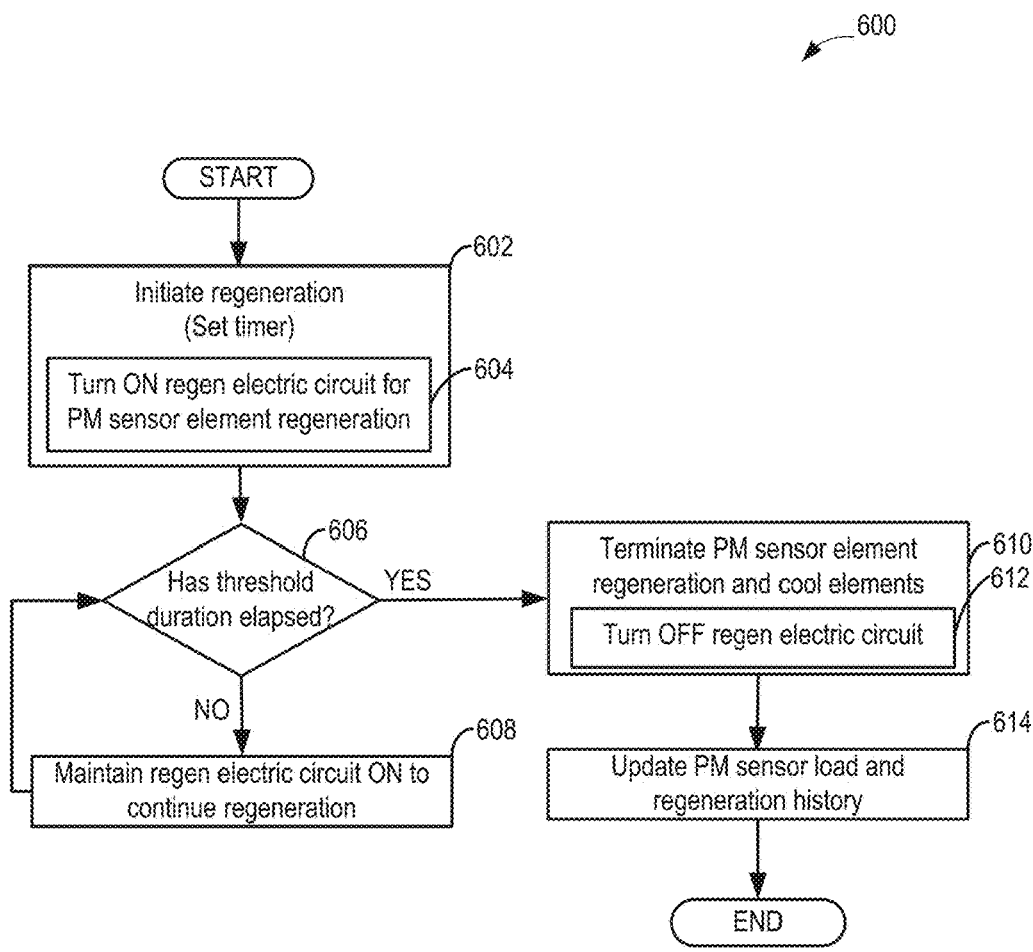
FIG. 6 a flow chart depicting an example method for regenerating the sensor electrodes of the PM sensor assembly.

If regeneration conditions are met (e.g., "YES" at 516), then method 500 proceeds to 520 where the PM sensor may be regenerated by performing a method described in FIG. 6. Briefly, regeneration of the PM sensor may be initiated by heating up the sensor. The PM sensor may be heated by actuating a heating element coupled thermally to the substrate of the sensor electrodes, for example. Herein, the controller may close the switch in a regeneration circuit, thereby applying a voltage to the heating element, causing the heating elements to heat up. Further, the controller may not apply voltages to the sensor electrodes while regenerating the sensor. Thus, the sensor electrodes may not accumulate soot during the sensor regeneration. As such, the heating element may be actuated until the soot load of the sensor has been sufficiently reduced by oxidation of the carbon particles between the electrodes. However, if PM sensor regeneration conditions are not met (e.g., "NO" at 516), then method proceeds to 518 where the particulates may continue to be collected on the sensor electrodes.

Thus, an example method includes directing a portion of exhaust gas in an exhaust passage into a particulate matter sensor in a direction opposite to exhaust flow in the exhaust passage via inlets in a step, guiding the portion of the exhaust gas into a first region, and spiraling the portion of the exhaust gas from the first region into a second region, the second region being fluidically coupled to the first region. The method may further include flowing the portion of the exhaust gas from the second region into a third region via a first slit on the third region towards sensor electrodes on a plate in a direction opposite to the exhaust flow in the exhaust passage, streaming the portion of the exhaust gas via a second slit positioned on the plate into a fourth region, the plate separating the third region and the fourth region, and steering the portion of the exhaust gas via a bottom surface of the fourth region towards the exhaust passage in a direction orthogonal to the exhaust flow in the exhaust passage. Additionally or alternatively, the first region and the second region may together form an outer asymmetric tube, and wherein the third region and the fourth region may together form an inner asymmetric tube, the inner asymmetric tube being positioned coaxially within the outer asymmetric tube. Additionally or alternatively, the inlets may guide the portion of the exhaust gas into the first region and not to any of the second region, third region, and the fourth region. Additionally or alternatively, a first longer axis of the first slit may be orthogonal to a second longer axis of the second slit, each of the first longer axis and the second longer axis being orthogonal to the direction of the exhaust flow in the exhaust passage.

Turning now to FIG. 6, a method 600 for regenerating the PM sensor (such as a PM sensor 106 shown at FIG. 1, and/or PM sensor assembly 201 of FIG. 2, for example) is shown. Specifically, when the soot load on the PM sensor is greater than the threshold, or when a resistance of the PM sensor adjusted for temperature drops to a threshold resistance, the PM sensor regeneration conditions may be considered met, and the PM sensor may require regeneration to enable further PM detection. At 602, regeneration of the PM sensor may be initiated and the PM sensor may be regenerated by heating up the sensor at 604. The PM sensor may be heated by actuating a heating element until the soot load of the sensor has been sufficiently reduced by oxidation of the carbon particles between the electrodes. The PM sensor regeneration is typically controlled by using timers and the timer may be set for a threshold duration at 602. Alternatively, the sensor regeneration may be controlled using a temperature measurement of the sensor tip, or by the control of power to the heater, or any or all of these. When a timer is used for PM sensor regeneration, then method 600 includes checking if the threshold duration has elapsed at 606. If the threshold duration has not elapsed (e.g., "NO" at 606), then method 600 proceeds to 608 where the regeneration circuit may be kept ON to continue regeneration. If threshold duration has elapsed (e.g., "YES" at 606), then method 600 proceeds to 610 where the PM sensor regeneration may be terminated and the electric circuit may be turned off at 612. Further, the sensor electrodes may be cooled to the exhaust temperature for example. Method 600 proceeds to 614 where the PM sensor load and regeneration history may be updated and stored in memory. For example, a frequency of PM sensor regeneration and/or an average duration between sensor regenerations may be updated and the method ends.

The engine exhaust passage may include one or more PM sensors positioned upstream and/or downstream of the DPF for determining a soot load of the DPF. When the PM sensor is positioned upstream of the DPF, based on the resistance change following soot deposited on the plurality of electrodes of the PM sensor, a soot load on the sensor may be inferred. The soot load thus determined, may be used to update the soot load on the DPF, for example. If the soot load on the DPF is greater than a threshold for DPF regeneration, then the controller may adjust engine operating parameters to regenerate the DPF. Specifically, responsive to filter regeneration conditions being met, a temperature of the filter (or in the vicinity of the filter) may be sufficiently raised to burn off stored soot. This may include operating a heater coupled to the DPF, or raising a temperature of engine exhaust (e.g., by operating rich) flowed into the DPF.

Figure 7:
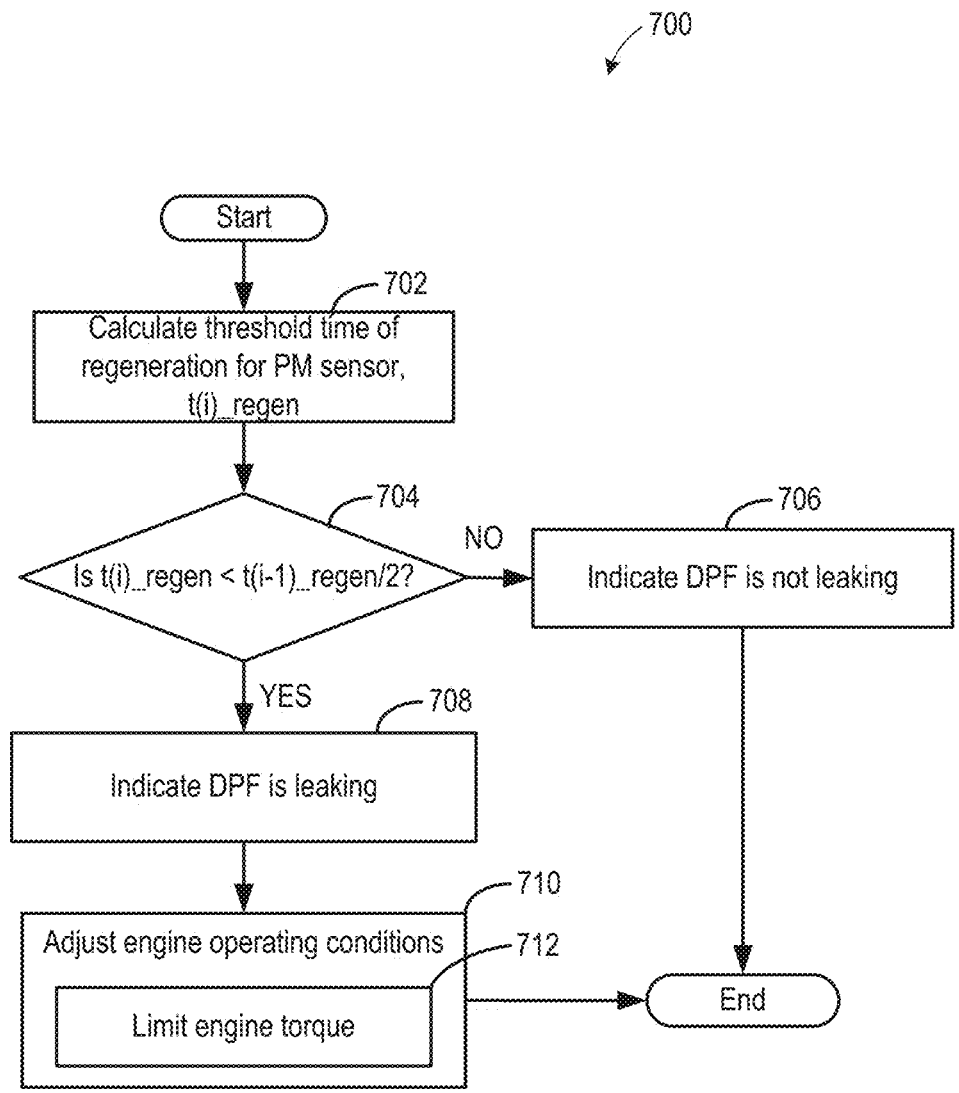
FIG. 7 shows a flow chart depicting an example method for diagnosing leaks in a particulate filter positioned upstream of the PM sensor assembly.
Figure 8:
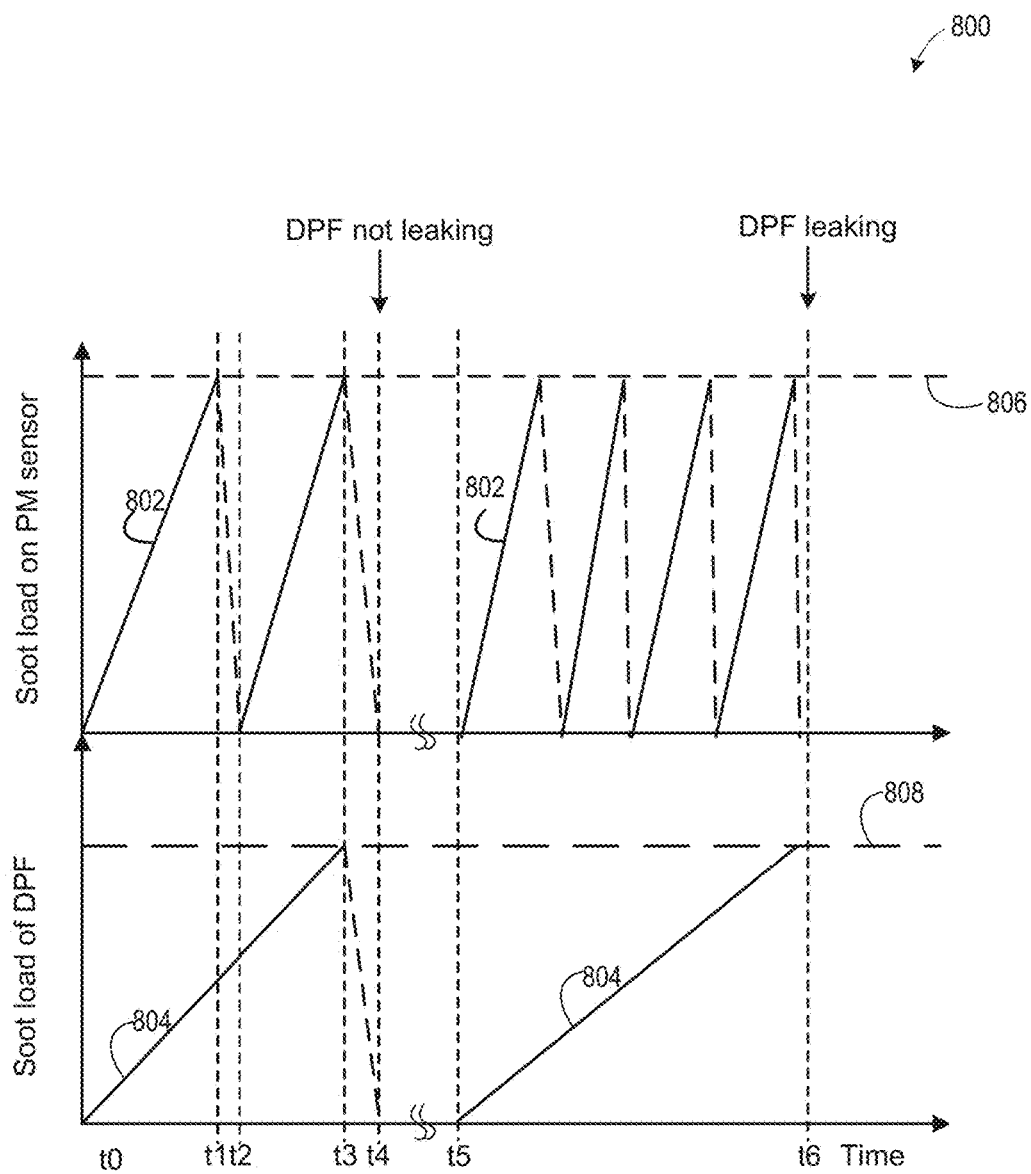
FIG. 8 shows an example relationship between a soot load on the PM sensor assembly, and a soot load on a particulate filter positioned upstream of the PM sensor assembly.

Turning now to FIG. 7, an example method 700 for diagnosing DPF function based on the regeneration time of the PM sensor is shown. At 702, it may be calculated by the controller, through calibration, the time of regeneration for the PM sensor, t(i)_regen, which is the time measured from end of previous regeneration to the start of current regeneration of the PM sensor. At 704, compare t(i)_regen to t(i−1)_regen, which is the previously calibrated time of regeneration of the PM sensor. From this, it may be inferred that the soot sensor may cycle through regeneration multiple times in order to diagnose the DPF. If the t(i)_regen is less than half the value of t(i−1) region, then at 708 indicate DPF is leaking, and DPF degradation signal is initiated. Alternatively, or additionally to the process mentioned above, the DPF may be diagnosed using other parameters, such as exhaust temperature, engine speed/load, etc. The degradation signal may be initiated by, for example, a malfunction indication light on diagnostic code. In addition, method 700 includes adjusting engine operation based on indicating leak in the DPF at 710. Adjusting engine operation may include limiting engine torque at 712, for example. In one example, responsive to detecting leak in the DPF, engine power and torque may be reduced. Reducing the engine power and torque may reduce the amount of PM emissions in the exhaust. For example, adjusting engine operation may include reducing fuel injected in a diesel engine under heavy load conditions thereby reducing torque. Additionally or alternatively, responsive to detecting leak in the DPF, an EGR usage may be decreased. Additionally or alternatively, an engine warning sign will appear on the dashboard to indicate the maximal distance vehicle can drive before DPF service check.

A current regeneration time of less than half of the previous regeneration time may indicate that the time for electric circuit to reach the R_regen threshold is significantly shorter, and thus the frequency of regeneration is higher. Higher frequency of regeneration in the PM sensor may indicate that the outflowing exhaust gas is composed of a higher amount of particulate matter than realized with a normally functionally DPF. Thus, if the change of regeneration time in the soot sensor reaches threshold, t_regen, in which the current regeneration time of the PM sensor is less than half of that of the previous regeneration time, a DPF degradation, or leaking, is indicated, for example via a display to an operator, and/or via setting a flag stored in non-transitory memory coupled to the processor, which may be sent to a diagnostic tool coupled to the processor. If the change in regeneration time of the soot sensor does not reach threshold t_regen, then at 706 DPF leaking is not indicated. In this way, leaks in a particulate filter positioned upstream of the particulate matter sensor may be detected based on a rate of deposition of the particulates on the particulate matter sensor electrodes.

Turning now to FIG. 8, map 800 shows an example relationship between soot load on the PM sensor and the soot load on the particulate filter. Specifically, map 800 shows a graphical depiction of the relationship between PM sensor regeneration and the soot load of the DPF, specifically how PM sensor regeneration may indicate DPF degradation. Vertical markers t0, t1, t2, t3, t4, t5 and t6 identify significant times in the operation and system of PM sensor and DPF.

The first plot of FIG. 8 shows a soot load on the PM sensor. As previously described, PM gets deposited across the positive and negative electrodes formed on a plate that is positioned inside a stepped assembly. As soot gets accumulated, a current measured across the electrodes beings to increase (or a resistance of the electrodes begins to decrease). The controller may be able to determine a soot load (plot 802) based on the current/resistance measured. As such, the soot load is at its lowest value at the bottom of the plots and increases in magnitude toward the top of the plot in the vertical direction. The horizontal direction represents time and time increases from the left to the right side of the plot. Horizontal marker 806 represents the threshold load for regeneration of the PM sensor in the top plot. Plot 804 represents the soot load on the DPF, and the horizontal marker 808 represents the threshold soot load of DPF in the second plot.

Between t0 and t1, a PM sensor regeneration cycle is shown. At time t0, the PM sensor is in a relatively clean condition, as measured by low PM load (plot 802). A controller coupled to the PM sensor determines the soot load of the PM sensor based on the current/resistance measured across the sensor electrodes, for example. When the controller determines the soot load to be small, it may send instructions to a regeneration circuit to end supplying heat, so that a detection circuit may begin detecting PM load accumulation. As PM load increases on the sensor, soot gets accumulated in the gap between the sensor electrodes.

Between t0 and t1, as PM continues to accumulate, the soot load (plot 802) increases accordingly and further soot load on DPF also increases (plot 804). In some examples, soot load on the DPF may be based on PM sensor load when PM sensor is located upstream of DPF, for example.

At t1, the soot load on the PM sensor (plot 802) reaches the threshold load for regeneration of the PM sensor (marker 806). The threshold load may a load at which the sensor may require regeneration. At t1, PM sensor regeneration may be initiated as explained earlier. Briefly, the controller may close a switch in the electric circuit to apply voltage to the heating elements formed along the inner surface of the central element, for example. In addition, the PM sensor may not be operated in PM accumulation mode, thus the controller may not apply any voltage to the sensor electrodes.

Thus, between t1 and t2, the PM sensor may be regenerated by turning on the electric circuit for regeneration. At t2, the PM sensor may be sufficiently cool, and may begin to accumulate soot and continue accumulating between t2 and t3 (DPF regeneration cycle), for example. During time between t2 and t3, DPF soot load continues to increase (plot 804). However, at t3, the soot load on the DPF (plot 804) reaches the threshold soot load for DPF regeneration (marker 808). Between t3 and t4, the DPF may be regenerated to burn off the soot deposited on the DPF. Further at t4, the PM sensor regeneration frequency may be compared with a previously estimated regeneration frequency of the PM sensor. Based on the PM sensor regeneration frequency remaining similar to previous cycles, the DPF may be determined to be not leaking. In this way, based on PM sensor output, DPF health may be monitored and diagnosed for leaks.

Between t5 and t6, another DPF cycle is shown. Herein, between t5 and t6, the soot load on the DPF gradually increases (plot 804). During this time, the soot load on the PM sensor (plot 802) may be monitored. Plot 802 shows the PM sensor going through multiple regeneration cycles as described earlier. However, the frequency of regeneration of the PM sensor has nearly doubled (plot 802). The higher frequency of regeneration in the PM sensor may indicate that the outflowing exhaust gas is composed of a higher amount of particulate matter than realized with a normally functional DPF. Therefore at t6, DPF leakage may be indicated.

In this way, a more accurate measure of the exhaust PM load, and thereby the DPF soot load can be determined. As such, this increases the efficiency of filter regeneration operations. In addition, by enabling more accurate diagnosis of an exhaust DPF, exhaust emissions compliance may be increased. As such, this reduces the high warranty costs of replacing functional particulate filters and exhaust component life is extended.

In this way, a sensor element may be shielded by two asymmetric protective tubes that further enhance uniform soot deposition. Exhaust gases may enter the sensor assembly via a step formed on the protection tube. As such, the exhaust may undergo changes in flow direction which helps reduce flow rate. Further, inlets on the tubes of the PM sensor assembly may be sized, shaped, and positioned to generate uniform flow of exhaust gases onto the sensor surface. A technical effect of greater uniform flow impingement of sample gasses on a particulate matter sensor may be achieved by decreasing the flow speed of the exhaust gas. Upon entering the first outer tube, exhaust gas may change direction and be forced up towards to the top of the sensor assembly, before entering intake apertures, and then may flow down, and out exit channels at the bottom of the sensor assembly. Thus, by interrupting the flow path of the exhaust gas, and decreasing its speed, the uniformity of the flow on the particulate matter sensor surface may be increased. Further still, by using the step to compel changes in gas flow direction, the particulate matter sensor may be shielded from contamination by larger particulates and water droplets. Thus, the step formed as a result of the asymmetry in the inner and outer tubes may act as a filter for the contaminants in the exhaust flow. As such, the contaminants may not be able to enter the PM sensor assembly. Thus, without adding additional components to the PM sensor assembly, the sensor electrodes positioned within the assembly may be protected from impingement of water droplets and larger particulates.

The systems and methods described above provide for a particulate matter sensor comprising an outer stepped tube having a first semi-circular region and a second semi-circular region, the first region being longer than the second region, an inner stepped tube coaxial to the outer stepped tube having a third semi-circular region and a fourth semi-circular region, the third region being longer than the fourth region, and a plate positioned inside the inner stepped tube having a sensor element. In a first example of the particulate matter sensor, the sensor may additionally or alternatively include wherein the inner stepped tube is positioned coaxially within the outer stepped tube and separated from the outer stepped tube by a gap, and wherein a top surface of the inner stepped is coplanar with a top surface of the outer stepped tube. A second example of the particulate matter sensor optionally includes the first example and further includes wherein the first region includes a first, sealed bottom surface and the second region includes a second, sealed bottom surface, the first bottom surface not coplanar with the second bottom surface. A third example of the particulate matter sensor optionally includes one or more of the first and the second examples, and further includes wherein the third region includes a third, unsealed bottom surface and the fourth region includes a fourth, sealed bottom surface, the third bottom surface not coplanar with the fourth bottom surface. A fourth example of the particulate matter sensor optionally includes one or more of the first through the third examples, and further includes wherein the first bottom surface is coplanar with the third bottom surface and the second bottom surface is coplanar with the fourth bottom surface. A fifth example of the particulate matter sensor optionally includes one or more of the first through the fourth examples, and further includes wherein the third region is positioned coaxially within the first region, each of the first region and the third region extending to a first distance in an exhaust pipe. A sixth example of the particulate matter sensor optionally includes one or more of the first through the fifth examples, and further includes wherein the fourth region is positioned coaxially within the second region, each of the second region and the fourth region extending to a second distance in the exhaust pipe. A seventh example of the particulate matter sensor optionally includes one or more of the first through the fifth examples, and further includes wherein a difference between the first distance and the second distance forms a step, a height of the step being substantially equal to the difference. An eighth example of the particulate matter sensor optionally includes one or more of the first through the seventh examples, and further includes wherein a length of the step is substantially equal to a diameter of the first region and the second region. A ninth example of the particulate matter sensor optionally includes one or more of the first through the eighth examples, and further includes wherein the step includes inlets that allow exhaust gas flowing in the exhaust pipe to reverse flow direction and enter via the inlets and into the gap between the inner stepped tube and the outer stepped tube. A tenth example of the particulate matter sensor optionally includes one or more of the first through the ninth examples, and further includes wherein the third region includes a first slit for flowing the exhaust gas from the gap into a first space enclosed between the plate and the fourth region; the first space including the sensor element. An eleventh example of the particulate matter sensor optionally includes one or more of the first through the tenth examples, and further includes wherein the plate includes a second slit for directing the exhaust gas from the first space into a second space enclosed between the plate and the third region, and further towards an exit in the third bottom surface.

The systems and methods described above also provide for a method of particulate matter sensing, in a particulate matter sensor system, the method comprising directing a portion of exhaust gas in an exhaust passage into a particulate matter sensor in a direction opposite to exhaust flow in the exhaust passage via inlets in a step, guiding the portion of the exhaust gas into a first region, spiraling the portion of the exhaust gas from the first region into a second region, the second region being fluidically coupled to the first region, flowing the portion of the exhaust gas from the second region into a third region via a first slit on the third region towards sensor electrodes on a plate in a direction opposite to the exhaust flow in the exhaust passage, streaming the portion of the exhaust gas via a second slit positioned on the plate into a fourth region, the plate separating the third region and the fourth region, and steering the portion of the exhaust gas via a bottom surface of the fourth region towards the exhaust passage in a direction orthogonal to the exhaust flow in the exhaust passage. In a first example of the method, the method may additionally or alternatively include wherein the first region and the second region together form an outer asymmetric tube, and wherein the third region and the fourth region together form an inner asymmetric tube, the inner asymmetric tube being positioned coaxially within the outer asymmetric tube. A second example of the method optionally includes the first example, and further includes wherein the inlets guide the portion of the exhaust gas into the first region and not to any of the second region, third region, and the fourth region. A third example of the method optionally includes one or more of the first and the second examples, and further includes wherein a first longer axis of the first slit is orthogonal to a second longer axis of the second slit, each of the first longer axis and the second longer axis being orthogonal to the direction of the exhaust flow in the exhaust passage.

The systems and methods described above provide for a system comprising a particulate matter (PM) sensor located downstream of a particulate filter in an exhaust passage, the PM sensor having an asymmetric protection tube including a step wherein the asymmetric protection tube includes a first segment coupled to a second segment, the first segment being longer than the second segment, and further wherein a difference in lengths between the first segment and the second segment generates the step. In a first example of the particulate matter sensor, the sensor may additionally or alternatively include wherein the first segment includes a first volume and a second volume, and wherein the second segment includes a third volume and a fourth volume, the first volume being fluidically coupled to the third volume. A second example of the particulate matter sensor optionally includes the first example and further comprising a first inlet on the step directing exhaust in the exhaust passage into the first volume and subsequently into the third volume, a second inlet steering the exhaust gas from the third volume into the fourth volume, the fourth volume including sensor elements positioned on a plate, the plate separating the third volume and the second volume, a third inlet on the plate flowing the exhaust gas from the fourth volume into the second volume, and an outlet on the first segment directing the exhaust gas from the second volume into the exhaust passage. A third example of the particulate matter sensor optionally includes one or more of the first and the second examples, and further comprising a controller with computer readable instructions stored on non-transitory memory for accumulating particulates in the exhaust on the sensor elements, determining a load on the PM sensor based on a current generated between the sensor elements, and responsive to the load being higher than a threshold, regenerate the PM sensor.

In another representation, an example method may include reversing an exhaust flow direction and streaming a portion of an exhaust gas flowing from a particulate filter into a particulate matter (PM) sensor assembly via inlet slits on a first surface of the PM sensor assembly, the first surface being a downstream surface, spiraling the portion of exhaust gas into a annular region of the PM sensor assembly, the annular region formed between an outer asymmetrical tube and an inner asymmetrical tube of the PM sensor assembly, directing the portion of the exhaust gas towards a sensor element formed on a plate positioned centrally within the PM sensor assembly via a rectangular slit on a downstream surface of the inner asymmetrical tube, flowing the portion of the exhaust gas through a perforation on the plate to an inner segment of the inner asymmetrical tube, and directing the portion of the exhaust gas through a bottom surface of the inner segment of the inner asymmetrical tube. Additionally or alternatively, the first surface may include a step orthogonal to an exhaust flow direction. Additionally or alternatively, the method may include accumulating PM on the sensor element, and further include regenerating the sensor element based on a PM load on the sensor element.

In yet another representation, a particulate matter sensor may include an outer protecting tube including a first cutout formed on a first portion of the outer tube, an inner tube positioned coaxially within the outer tube having a second cutout on a second portion of the inner tube, the second portion being proximate to the first portion; and a central plate having sensor elements, the central plate separating the inner tube into two segments.

Note that the example control and estimation routines included herein can be used with various engine and/or vehicle system configurations. The control methods and routines disclosed herein may be stored as executable instructions in non-transitory memory and may be carried out by the control system including the controller in combination with the various sensors, actuators, and other engine hardware. The specific routines described herein may represent one or more of any number of processing strategies such as event-driven, interrupt-driven, multi-tasking, multi-threading, and the like. As such, various actions, operations, and/or functions illustrated may be performed in the sequence illustrated, in parallel, or in some cases omitted. Likewise, the order of processing is not necessarily required to achieve the features and advantages of the example embodiments described herein, but is provided for ease of illustration and description. One or more of the illustrated actions, operations and/or functions may be repeatedly performed depending on the particular strategy being used. Further, the described actions, operations and/or functions may graphically represent code to be programmed into non-transitory memory of the computer readable storage medium in the engine control system, where the described actions are carried out by executing the instructions in a system including the various engine hardware components in combination with the electronic controller.

It will be appreciated that the configurations and routines disclosed herein are exemplary in nature, and that these specific embodiments are not to be considered in a limiting sense, because numerous variations are possible. For example, the above technology can be applied to V-6, I-4, I-6, V-12, opposed 4, and other engine types. The subject matter of the present disclosure includes all novel and non-obvious combinations and sub-combinations of the various systems and configurations, and other features, functions, and/or properties disclosed herein. The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

The invention claimed is:

1. A particulate matter sensor assembly, comprising:
an outer stepped tube having a first semi-circular region and a second semi-circular region, the first region being longer than the second region;
an inner stepped tube coaxial to the outer stepped tube having a third semi-circular region and a fourth semi-circular region, the third region being longer than the fourth region; and
a plate positioned inside the inner stepped tube having a sensor element.

2. The particulate matter sensor assembly of claim 1, wherein the inner stepped tube is positioned coaxially within the outer stepped tube and separated from the outer stepped tube by a gap, and wherein a top surface of the inner stepped tube is coplanar with a top surface of the outer stepped tube.

3. The particulate matter sensor assembly of claim 2, wherein the third region is positioned coaxially within the first region, each of the first region and the third region extending to a first distance in an exhaust pipe.

4. The particulate matter sensor assembly of claim 3, wherein the fourth region is positioned coaxially within the second region, each of the second region and the fourth region extending to a second distance in the exhaust pipe.

5. The particulate matter sensor assembly of claim 4, wherein a difference between the first distance and the second distance forms a step, a height of the step being substantially equal to the difference.

6. The particulate matter sensor assembly of claim 5, wherein a length of the step is substantially equal to a diameter of the first region and the second region.

7. The particulate matter sensor assembly of claim 5, wherein the step includes inlets that allow exhaust gas flowing in the exhaust pipe to reverse flow direction and enter via the inlets and into the gap between the inner stepped tube and the outer stepped tube.

8. The particulate matter sensor assembly of claim 7, wherein the third region includes a first slit for flowing the exhaust gas from the gap into a first space enclosed between the plate and the fourth region, the first space including the sensor element.

9. The particulate matter sensor assembly of claim 8, wherein the plate includes a second slit for directing the exhaust gas from the first space into a second space enclosed between the plate and the third region, and further towards an exit in a third bottom surface.

10. The particulate matter sensor assembly of claim 1, wherein the first region includes a first, sealed bottom surface and the second region includes a second, sealed bottom surface, the first bottom surface not coplanar with the second bottom surface.

11. The particulate matter sensor assembly of claim 10, wherein the third region includes a third, unsealed bottom surface and the fourth region includes a fourth, sealed bottom surface, the third bottom surface not coplanar with the fourth bottom surface.

12. The particulate matter sensor assembly of claim 11, wherein the first bottom surface is coplanar with the third bottom surface and the second bottom surface is coplanar with the fourth bottom surface.

13. A system, comprising:
a particulate matter (PM) sensor located downstream of a particulate filter in an exhaust passage, the PM sensor having an asymmetric protection tube including a step, wherein the asymmetric protection tube includes a first segment separated from a second segment by a plate including a plate inlet, the first segment being longer than the second segment, and further wherein a difference in length between the first segment and the second segment generates the step.

14. The system of claim 13, wherein the first segment includes a first volume and a second volume, and wherein the second segment includes a third volume and a fourth volume, the first volume being fluidically coupled to the third volume.

15. The system of claim 14, further comprising a first inlet on the step directing exhaust gas in the exhaust passage into the first volume and subsequently into the third volume;
a second inlet steering the exhaust gas from the third volume into the fourth volume, the fourth volume including sensor elements positioned on the plate and the plate separating the third volume and the second volume;
the plate inlet flowing the exhaust gas from the fourth volume into the second volume; and
an outlet on the first segment directing the exhaust gas from the second volume into the exhaust passage.

16. The system of claim 15, further comprising a controller with computer readable instructions stored on non-transitory memory for:
accumulating particulates in the exhaust gas on the sensor elements;
determining a load on the PM sensor based on a current generated between the sensor elements; and
responsive to the load being higher than a threshold, regenerating the PM sensor.

* * * * *